US009614337B2

(12) United States Patent
Lisogurski et al.

(10) Patent No.: US 9,614,337 B2
(45) Date of Patent: Apr. 4, 2017

(54) MULTIPLE ORIENTATION CONNECTORS FOR MEDICAL MONITORING SYSTEMS

(71) Applicant: COVIDIEN LP, Mansfield, MA (US)

(72) Inventors: Daniel Lisogurski, Boulder, CO (US); Christopher J. Meehan, Arvada, CO (US); Timothy W. Fries, Louisville, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/738,333

(22) Filed: Jun. 12, 2015

(65) Prior Publication Data

US 2015/0372433 A1 Dec. 24, 2015

Related U.S. Application Data

(60) Provisional application No. 62/014,374, filed on Jun. 19, 2014.

(51) Int. Cl.
| | | |
|---|---|---|
| *H01R 27/00* | (2006.01) | |
| *H01R 29/00* | (2006.01) | |
| *H01R 24/28* | (2011.01) | |
| *A61B 5/1455* | (2006.01) | |

(52) U.S. Cl.
CPC ......... *H01R 29/00* (2013.01); *A61B 5/14552* (2013.01); *H01R 24/28* (2013.01); *A61B 2560/0456* (2013.01); *A61B 2562/227* (2013.01)

(58) Field of Classification Search
CPC .... H01R 29/00; H01R 24/28; A61B 5/14552; A61B 2560/0456; A61B 2562/227; A61B 5/1455

USPC ................................... 439/224, 692
See application file for complete search history.

(56) References Cited

U.S. PATENT DOCUMENTS

| | | | |
|---|---|---|---|
| 4,700,708 | A | 10/1987 | New, Jr. et al. |
| 4,964,408 | A | 10/1990 | Hink et al. |
| 5,069,213 | A | 12/1991 | Polczynski |
| 5,154,175 | A | 10/1992 | Gunther |
| 5,228,440 | A | 7/1993 | Chung et al. |
| 5,249,576 | A | 10/1993 | Goldberger et al. |

(Continued)

FOREIGN PATENT DOCUMENTS

| | | |
|---|---|---|
| JP | 6016774 | 3/1994 |
| JP | 2004329406 | 11/2004 |

(Continued)

OTHER PUBLICATIONS

Annex to Invitation to Pay Additional Fees for PCT Application No. PCT/US2015/036264 mailed Aug. 27, 2015, 5 pages.

(Continued)

*Primary Examiner* — Javaid Nasri
(74) *Attorney, Agent, or Firm* — Fletcher Yoder PC

(57) ABSTRACT

A connector for coupling a medical sensor to a medical monitor includes a first pin coupled and a second pin each electrically coupled to a first LED and to a second LED, respectively, of an emitter of the medical sensor. The connector includes a third pin electrically coupled to a cathode and a fourth pin electrically coupled to an anode of a detector of the medical sensor. The first pin and the second pin are arranged to have 180 degree symmetry relative to one another, and the third pin and the fourth pin are arranged to have 180 degree symmetry relative to one another.

20 Claims, 12 Drawing Sheets

(56) References Cited

U.S. PATENT DOCUMENTS

| | | | |
|---|---|---|---|
| 5,287,853 | A | 2/1994 | Vester et al. |
| 5,343,869 | A | 9/1994 | Pross et al. |
| 5,387,122 | A | 2/1995 | Goldberger et al. |
| 5,491,299 | A | 2/1996 | Naylor et al. |
| 5,603,623 | A | 2/1997 | Nishikawa et al. |
| 5,645,440 | A | 7/1997 | Tobler et al. |
| 5,660,567 | A | 8/1997 | Nierlich et al. |
| 5,743,260 | A | 4/1998 | Chung et al. |
| 5,790,729 | A | 8/1998 | Pologe et al. |
| 5,817,008 | A | 10/1998 | Rafert et al. |
| 5,851,178 | A | 12/1998 | Aronow |
| 5,890,929 | A | 4/1999 | Mills et al. |
| 5,934,925 | A | 8/1999 | Tobler et al. |
| 5,961,452 | A | 10/1999 | Chung et al. |
| 5,997,343 | A | 12/1999 | Mills et al. |
| 6,014,576 | A | 1/2000 | Raley |
| 6,026,312 | A | 2/2000 | Shemwell et al. |
| 6,112,107 | A | 8/2000 | Hannula |
| 6,152,754 | A | 11/2000 | Gerhardt et al. |
| 6,165,005 | A | 12/2000 | Mills et al. |
| 6,253,097 | B1 | 6/2001 | Aronow et al. |
| 6,280,213 | B1 | 8/2001 | Tobler et al. |
| 6,370,409 | B1 | 4/2002 | Chung et al. |
| 6,541,756 | B2 | 4/2003 | Schulz et al. |
| 6,678,543 | B2 | 1/2004 | Diab et al. |
| 6,850,788 | B2 | 2/2005 | Al-Ali |
| 7,117,590 | B2 | 10/2006 | Koenig et al. |
| 7,132,641 | B2 | 11/2006 | Schulz et al. |
| 7,210,959 | B1 | 5/2007 | Teves |
| 7,371,981 | B2 | 5/2008 | Abdul-Hafiz |
| 7,427,165 | B2 | 9/2008 | Benaron et al. |
| 7,486,979 | B2 | 2/2009 | Matlock |
| 8,517,766 | B2 | 8/2013 | Golko et al. |
| 8,535,075 | B1 | 9/2013 | Golko et al. |
| 8,556,659 | B1 | 10/2013 | Rothkopf et al. |
| 2002/0103423 | A1 | 8/2002 | Chin et al. |
| 2003/0109772 | A1 | 6/2003 | Mills |
| 2003/0135099 | A1 | 7/2003 | Al-Ali |
| 2003/0162414 | A1 | 8/2003 | Schulz et al. |
| 2003/0229276 | A1 | 12/2003 | Sarussi et al. |
| 2004/0267103 | A1 | 12/2004 | Li et al. |
| 2005/0113704 | A1 | 5/2005 | Lawson et al. |
| 2005/0131282 | A1 | 6/2005 | Brodnick et al. |
| 2006/0211932 | A1 | 9/2006 | Al-Ali et al. |
| 2006/0241363 | A1 | 10/2006 | Al-Ali et al. |
| 2007/0123783 | A1 | 5/2007 | Chang |
| 2008/0064940 | A1 | 3/2008 | Raridan |
| 2008/0071153 | A1 | 3/2008 | Al-Ali et al. |
| 2008/0081508 | A1 | 4/2008 | Sawatari et al. |
| 2008/0081954 | A1 | 4/2008 | Meyer et al. |
| 2008/0119076 | A1 | 5/2008 | Teicher |
| 2008/0316488 | A1 | 12/2008 | Mao et al. |
| 2010/0249540 | A1 | 9/2010 | Lisogurski |
| 2011/0034783 | A1* | 2/2011 | Lisogurski ........... A61B 5/0002 600/301 |
| 2011/0077473 | A1 | 3/2011 | Lisogurski |
| 2013/0115817 | A1 | 5/2013 | Terlizzi et al. |
| 2013/0117470 | A1 | 5/2013 | Terlizzi et al. |
| 2013/0134989 | A1 | 5/2013 | Cloutier et al. |
| 2014/0275873 | A1 | 9/2014 | Fries et al. |

FOREIGN PATENT DOCUMENTS

| | | |
|---|---|---|
| JP | 2005052385 | 3/2005 |
| JP | 2007117641 | 5/2007 |

OTHER PUBLICATIONS

International Search Report and Written Opinion for PCT Application No. PCT/US2015/036264 mailed Nov. 6, 2015, 17 pages.

Odagiri, Y.; "Pulse Wave Measuring Device," Micromechatronics, vol. 42, No. 3, pp. 6-11 (published Sep. 1998) (Article in Japanese—contains English summary of article).

Hayoz, J., et al.; "World's First Combined digital Pulse Oximetry Pulse Oximetry and Carbon Dioxide Tension Ear Sensor", Anesthesia & Analgesia 2002; 94: S103.

Aoyagi, Takuo; "Pulse oximetry: its invention, theory, and future," Journal of Anesthesia, vol. 17, pp. 259-266 (2003).

Avidan, A.; "Pulse oximeter ear probe," Anaesthesia, vol. 58, pp. 726 (2003).

Bentley, David J. et al.; "Measure Pressure with Thin Film"; Paper Film & Foil Converter; May 1, 2003.

Cyrill, D., et al.; "Adaptive Comb Filter for Quasi-Periodic Physiologic Signals," Proceedings of the 25th Annual International Conference of the IEEE EMBS, Cancun, Mexico, Sep. 17-21, 2003; pp. 2439-2442.

Itoh, K., et al.; "Pulse Oximeter," Toyaku Zasshi (Toyaku Journal), vol. 25, No. 8, pp. 50-54 (2003) (Article in Japanese—contains English summary of article).

Lebak, J.W., et al.; "Implementation of a Standards-Based Pulse Oximeter on a Wearable, Embedded Platform," Proceeding of the 25th Annual International Conference of the IEEE EMBS, Cancun, Mexico, Sep. 17-21, 2003; pp. 3196-3198.

Matsui, A., et al.; "Pulse Oximeter," Neonatal Care, vol. 16, No. 3, pp. 38-45 (2003) (Article in Japanese—contains English summary of article).

Nakagawa, M., et al.; "Oxygen Saturation Monitor," Neonatal Monitoring, vol. 26, No. 5, pp. 536-539 (2003) (Article in Japanese—contains English summary of article).

Nagl, L., et al.; "Wearable Sensor System for Wireless State-of-Health Determination in Cattle," Proceeding of the 25th Annual International Conference of the IEEE EMBS, Cancun, Mexico, Sep. 17-21, 2003; pp. 3012-3015.

Pujary, C., et al.; "Photodetector Size Considerations in the Design of a Noninvasive Reflectance Pulse Oximeter for Telemedicine Applications," IEEE, pp. 148-149 (2003).

Branche, Paul C., et al.; "Measurement Reproducibility and Sensor Placement Considerations in Designing a Wearable Pulse Oximeter for Military Applications," 2 pgs. (2004).

Heuss, Ludwig T., et al.; "Combined Pulse Oximetry / Cutaneous Carbon dioxide Tension Monitoring During Colonoscopies: Pilot study with a Smart Ear Clip," Digestion, vol. 70, pp. 152-158 (2004).

Johnston, William S., et al.; "Effects of Motion Artifacts on helmet-Mounted Pulse Oximeter Sensors," 2 pgs. (2004).

Kocher, Serge, et al.; "Performance of a Digital PCO2/SPO2 Ear Sensor," Journal of Clinical Monitoring and Computing, vol. 18, pp. 75-59 (2004).

Mannheimer, Paul D., et al.; "The influence of Larger Subcutaneous Blood Vessels on Pulse Oximetry," Journal of clinical Monitoring and Computing, vol. 18, pp. 179-188 (2004).

Matsuzawa, Y., et al.; "Pulse Oximeter," Home Care Medicine, pp. 42-45 (Jul. 2004); (Article in Japanese—contains English summary of article).

Reuss, James L.; "Factors Influencing Fetal Pulse Oximetry Performance," Journal of clinical Monitoring and Computing, vol. 18, pp. 13-14 (2004).

Sugino, Shigekzau, et al.; "Forehead is as sensitive as finger pulse oximetry during general anesthesia," Can J. Anesth.; General Anesthesia, vol. 51, No. 5; pp. 432-436 (2004).

Wendelkin, Suzanne, et al.; "The Feasibility of Using a Forehead Reflectance Pulse Oximeter for Automated Remote Triage," IEEE, pp. 180-181 (2004).

Urquhart, C., et al.; "Ear probe pulse oximeters and neonates," Anaesthesia, vol. 60, p. 294 (2005).

Goldman, Joshua; "Apple's lightning connector and you: What you should know," CNET Reviews Sep. 19, 2012, 3 pages.

http://www.cfw.com.my/fujifilm2.htm (accessed Jun. 25, 2008).

* cited by examiner

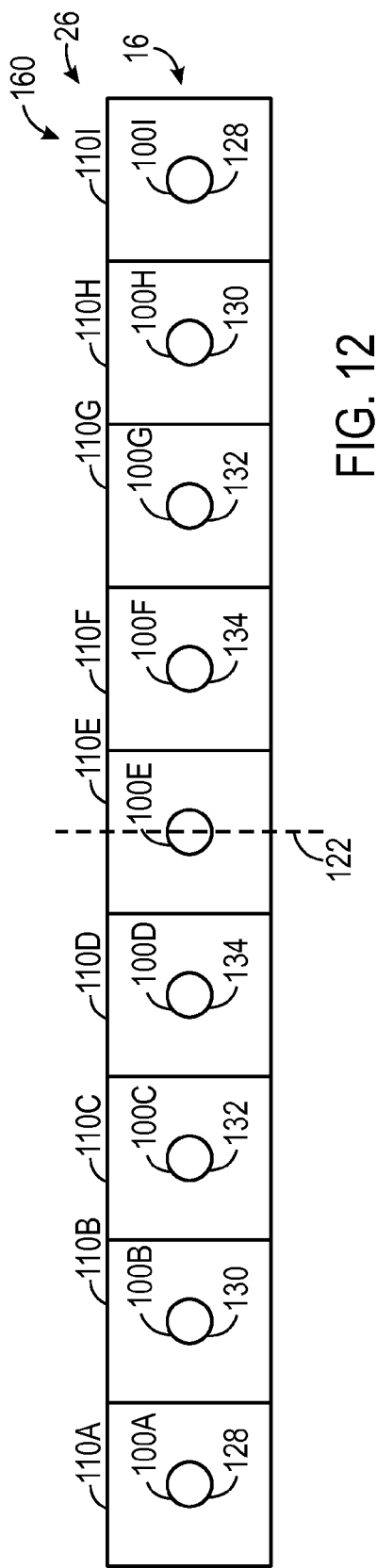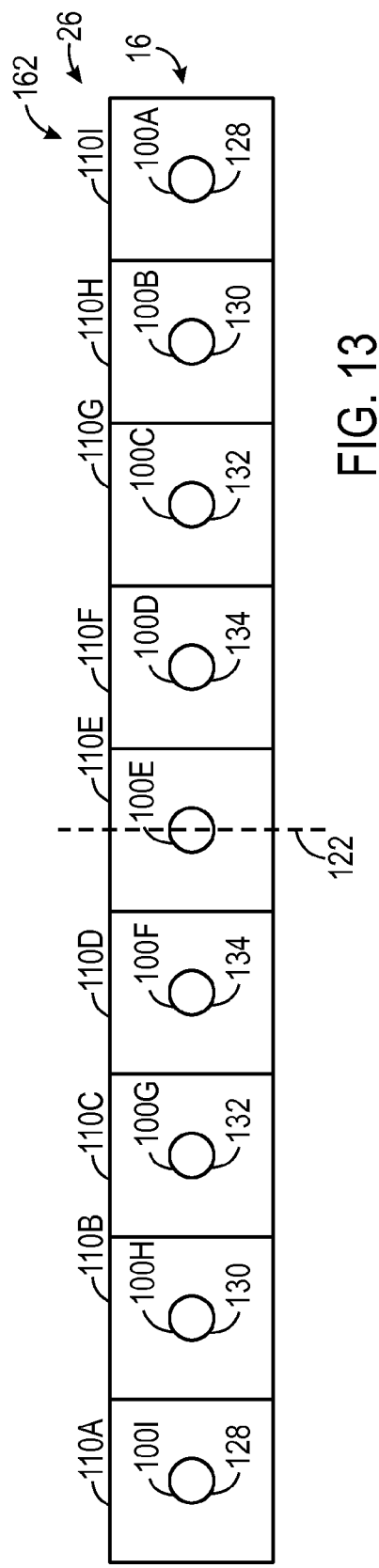

MULTIPLE ORIENTATION CONNECTORS FOR MEDICAL MONITORING SYSTEMS

CROSS REFERENCE TO RELATED APPLICATION

This application claims priority from and the benefit of U.S. Provisional Patent Application No. 62/014,374, filed Jun. 19, 2014, entitled "Multiple Orientation Connectors for Medical Monitoring Systems," which is incorporated by reference herein in its entirety.

BACKGROUND

The present disclosure relates generally to medical monitoring systems and, more particularly, to connectors for coupling a medical device such as a sensor to a monitor.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring certain physiological characteristics of a patient. Such devices provide doctors and other healthcare personnel with the information they need to provide the best possible healthcare for their patients. As a result, such monitoring devices have become an indispensable part of modern medicine. For example, photoplethysmography is a common technique for monitoring physiological characteristics of a patient, and one device based upon photoplethysmography techniques is commonly referred to as a pulse oximeter. The pulse oximeter may be used to measure and monitor various blood flow characteristics and/or physiological characteristics of a patient, such as the blood oxygen saturation of hemoglobin in arterial blood, the volume of individualized blood pulsations supplying the tissue, and/or the rate of blood pulsations corresponding to each heartbeat of the patient. In fact, the "pulse" in pulse oximetry refers to the time-varying amount of arterial blood in the tissue during each cardiac cycle.

A patient in a hospital setting may be monitored by a variety of medical devices, including devices based on pulse oximetry techniques. For example, a patient may be monitored with a pulse oximeter. Depending on the patient's clinical condition, a physician may monitor a patient with a regional oxygen saturation sensor to determine if the patient is at risk of hypoxia. If a patient is scheduled for surgery, additional or alternative monitoring devices may be applied. For example, one such device may include a bispectral index (BIS) sensor to measure the level of consciousness by algorithmic analysis of a patient's electroencephalography (EEG) during general anesthesia.

Various medical devices, such as sensors, are typically coupled to a monitor by a connector. However, typical connectors are oriented in one particular orientation to successfully couple the medical device to the monitor, which is inconvenient and may lead to delays in patient care. Additionally, each type of medical device and/or each type of monitor typically requires a different type of connector. The many different connectors that are required in the medical setting are also inconvenient for the medical practitioner, and the time required to identify and to orient the particular connector and/or to learn how to operate the various connectors may result in delays in patient care.

BRIEF DESCRIPTION OF THE DRAWINGS

Advantages of the disclosed techniques may become apparent upon reading the following detailed description and upon reference to the drawings in which:

FIG. 12 is a schematic diagram of a multiple orientation connector having a one-dimensional array of nine pins inserted within a receptacle of a monitor in a first orientation, in accordance with an embodiment;

FIG. 13 is a schematic diagram of the multiple orientation connector of FIG. 10 inserted within the receptacle of the monitor in a second orientation, in accordance with an embodiment;

DETAILED DESCRIPTION OF SPECIFIC EMBODIMENTS

Figure 1:
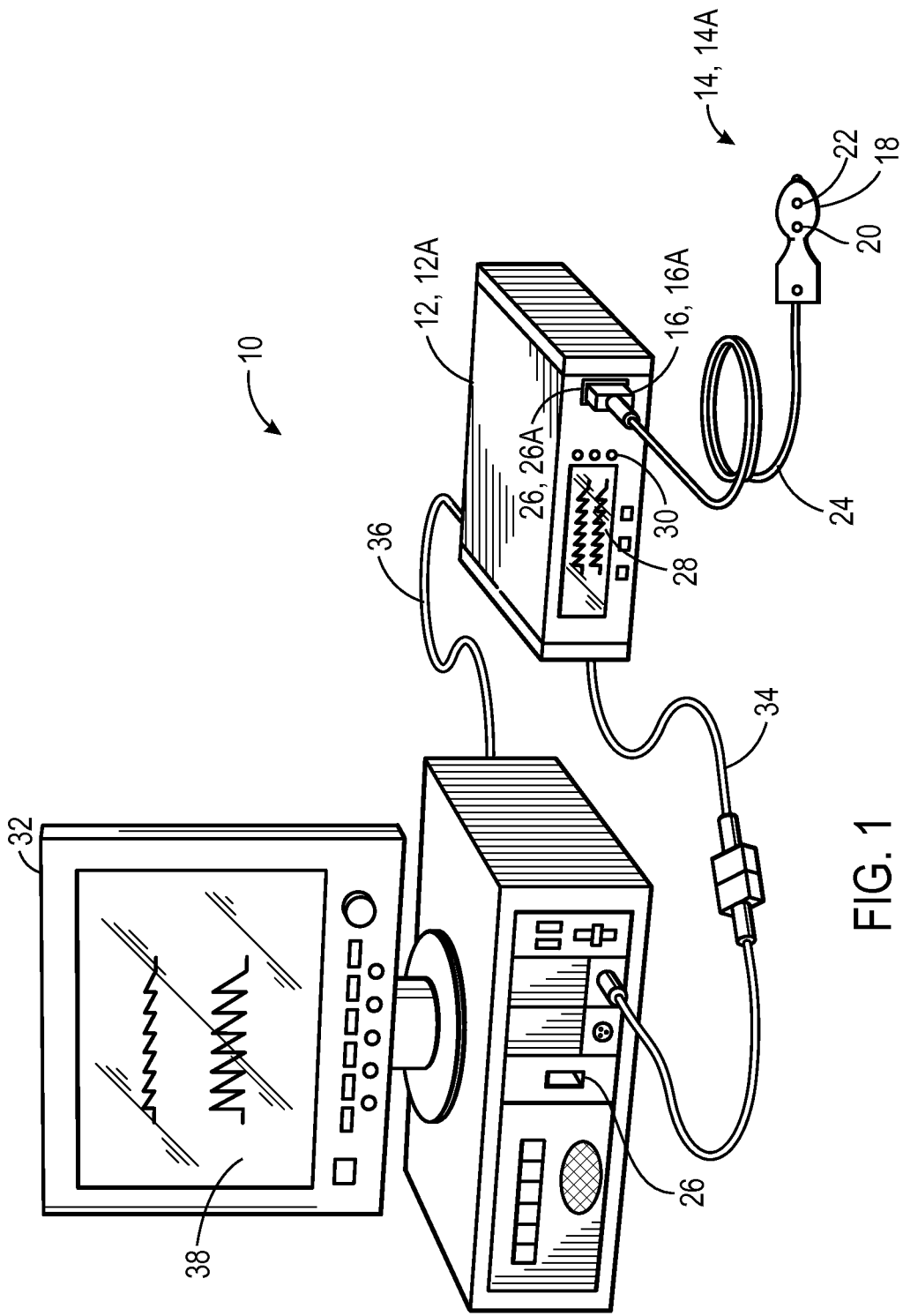
FIG. 1 is a front perspective view of an embodiment of a pulse oximetry monitoring system.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure is generally directed to connectors for coupling a medical device such as a sensor to a monitor. The described connectors may be multiple orientation connectors. That is, the connectors may be configured to mechanically and electrically couple the medical device to the monitor while the connector is in more than one orientation with respect to the monitor. For example, the connector may be a plug connector that is configured to be inserted into a receptacle of the monitor with a first side of the connector facing up or with the first side of the connector facing down. Further, the monitor may be configured to determine the orientation of the connector based on an interaction (e.g., a transfer or an exchange of electrical signals, or a mechanical interaction, such as a mechanically closing switch) between the receptacle of the monitor and the connector and/or the medical device that is coupled to the connector. In some cases, the monitor may be configured to remap or to adjust a function of electrical contacts of the receptacle based on the determined orientation of the connector, for example. Additionally, the connectors described herein may be compatible with a variety of medical devices, such as a variety of medical sensors, and/or a variety of monitors. For example, the connectors may be utilized to couple pulse oximetry sensors, regional oxygen saturation sensors, and/or electroencephalography (EEG) sensors to various monitors, such as pulse oximeter monitors, regional oxygen saturation monitors, EEG monitors, electrocardiography (ECG) monitors, electromyography (EMG) monitors, capnography monitors, and/or multi-parameter monitors.

Connectors in accordance with the present disclosure may provide certain advantages over traditional connectors. For example, the connector's reversibility, or ability to be inserted into the receptacle of the monitor in more than one orientation, may provide convenience and may save time in medical settings. Such time savings may, in turn, improve patient care. Furthermore, connectors that can be used with multiple different types of medical devices and/or monitor may provide cost savings or result in less equipment in already cluttered care facilities or vehicles used for patient transport. For example, a single medical device with a single receptacle may have two or more supported functions (pulse oximeter or regional saturation monitor), depending on the type of sensor plugged in to the receptacle. Additionally, connectors that can connect a medical device to a variety of monitors may provide convenience in the medical setting, as the operator may connect the medical device to a first type of monitor and may conveniently connect the medical device to a second type of monitor should the patient be moved or should a different type of monitor and/or display be desired, for example. Such connectors may also improve the functionality of patient monitoring systems, as a medical device may be easily coupled to various monitors, which may be configured to process, display, and/or store the data from the sensor in different manners. Furthermore, the uniform external appearance and configuration of the connectors may make the connectors relatively easy to recognize and operate in the fast-paced medical setting. More particularly, such connectors may reduce the amount of time required to couple the medical device to the monitor, as the operator does not have to identify and determine how to operate the particular connector being used. Additionally, medical personnel would not have to learn how to operate or be familiar with numerous different types of connectors.

Although the present application generally describes the connector as a plug connector (e.g., a male connector) that is coupled or attached to the medical sensor and that is configured to be inserted into a receptacle (e.g., a receptacle connector or a female connector) of the monitor to facilitate explanation and to simplify discussion, it should be understood that the connector and/or corresponding components of the monitor may have any suitable form for mechanically and electrically coupling the medical device to the monitor. Furthermore, while the present application generally describes the electrical contacts of the connector as pins, it should be understood that the electrical contacts may have any suitable form, such as electrically conductive pads of a printed circuit board, for example.

With the foregoing in mind, FIG. 1 depicts an embodiment of a patient monitoring system 10 that includes a patient monitor 12 that may be coupled to a medical device, such as a sensor 14, via a connector 16 (e.g., a multiple orientation connector). In the particular embodiment of FIG. 1, the monitor 12 is a pulse oximetry monitor 12A, the sensor 14 is a pulse oximetry sensor 14A, and the connector 16 is a pulse oximetry connector 16A. The pulse oximetry sensor 14A may include a sensor body 18, which may provide a structural support for the various components (e.g., sensing components) of the pulse oximetry sensor 14A, such as emitters 20 and detectors 22.

The connector 16 may be coupled to the sensor 14 in any suitable manner. For example, the connector 16 may be attached (e.g., permanently affixed) to the sensor 14. In certain embodiments, the connector 16 may be removably (e.g., releasably) coupled to the sensor body 18. Thus, the connector 16 may be a separate component of the monitoring system 10. When the connector 16 is attached or removably coupled to the sensor 14, together the connector 16 and the sensor 14 may form a sensor assembly. Further, as shown, the connector 16 may include a cable 24 that attaches or couples the connector 16 to the sensor 14, providing flexibility between the connector 16 and the sensor body 18, for example. The cable 24 may be of any suitable length to facilitate the coupling of the sensor 14 and the monitor 12 via the connector 16. In certain embodiments, the connector 16 may not include the cable 24.

Regardless of the manner in which the connector 16 is coupled to the sensor 14, the connector 16 may be configured to fit within a receptacle 26 (e.g., a receptacle connector, port, aperture, female connector, or the like), which may be disposed in the monitor 12. In FIG. 1, the receptacle 26 is a pulse oximetry receptacle 26A. The receptacle 26 may have a geometry (e.g., a shape) that corresponds to the connector 16 and enables the receptacle 26 to receive at least a portion of the connector 16. The matching shapes enable the connector 16 to mate with the receptacle 26, defining a mating interface where the two meet. In embodiments described further herein, this interface is symmetric, enabling the connector 16 and receptacle 26 to operate together in more than one configuration. In certain embodiments, the monitor 12 may not have the proper receptacle 26 for receiving the connector 16. In such cases, an adapter (e.g., a dongle) may be provided to facilitate coupling of the connector 16 to the monitor 12, by mating with the receptacle 26 on one end and the connector 16 on the opposite end.

When coupled together, the connector 16 and the receptacle 26 may facilitate the exchange of information between the monitor 12 and the sensor 14. More particularly, sensor 14 may provide electrical signals representative of various data, such as physiological data, to the monitor 12 via the connector 16. In some embodiments, the sensor 14 may process the signals and may provide physiological information or parameters to the monitor 12 via the connector 16. Additionally, the monitor 12 may provide instructions and/or operational parameters to the sensor 14 via the connector 16. For example, the monitor 12 may provide light drive signals to illuminate the emitters 20 of the sensor 14 via the connector 16. The monitor 12 may include a monitor display 28 configured to display information regarding the physiological parameters, information about the system, and/or alarm indications, for example. The monitor 12 may also include various input components 30, such as knobs, switches, keys and keypads, buttons, etc., to provide for operation and configuration of the monitor 12 and monitoring system 10. As noted above, the monitor 12 may be configured to receive electrical signals from the sensor 14 via the connector 16, and the monitor 12 may be configured to process the received signals to calculate various physiological parameters, such as oxygen saturation, for example.

The monitor 12 may also be coupled to a multi-parameter monitor 32 via a cable 34 connected to a sensor input port or via a cable 36 connected to a digital communication port. In addition to the monitor 12, or alternatively, the multi-parameter monitor 32 may be configured to calculate physiological parameters and to provide a central display 38 for visualization of information from the monitor 12 and from other medical devices, monitors, and/or monitoring systems. The multi-parameter monitor 32 may facilitate presentation of patient data, such as pulse oximetry data determined by the system 10 and/or physiological parameters determined by other patient monitoring systems (e.g., regional oxygen saturation monitor systems, bispectral index or electrocardiographic (ECG) monitoring system, a respiration monitoring system, a blood pressure monitoring system, etc.). For example, the multi-parameter monitor 32 may display a graph of $SpO_2$ values, a current pulse rate, a graph of blood pressure readings, an electrocardiograph, and/or other related patient data in a centralized location for quick reference by a medical professional. Although cables 34 and 36 are illustrated, it should be understood that the monitor 12 may be in wireless communication with the multi-parameter monitor 32. Additionally, the multi-parameter monitor 32 may take any suitable form. For example, the multi-parameter monitor 32 may be portable and/or relatively compact. In certain embodiments, the multi-parameter monitor 32 may have all of the functionality of the pulse oximetry monitor 12A, as well as additional functionality of any monitor 12 described herein.

In some embodiments, the multi-parameter monitor 32 may have the receptacle 26 configured to receive the connector 16. In such configurations, the sensor 14 may be directly coupled to the multi-parameter monitor 32 via the connector 16, and the sensor 14 may directly transmit electrical signals to the multi-parameter monitor 32 via the connector 16. In some embodiments, the multi-parameter monitor 32 may include a plurality of receptacles 26 to enable the multi-parameter monitor 32 to be coupled to a plurality of sensors 14 via a plurality of connectors 16 (e.g., a plurality of sensors 14 applied to a patient, a plurality of sensors 14 applied to a variety of patients, and/or a plurality of sensors 14 for the purposes of downloading settings or operational parameters to the different sensors 14, for example, may be connected to the multi-parameter monitor 32 via connectors 16). The connectors 16 and corresponding receptacles 26 may enable various combinations of different types of sensors 14 to be readily and easily coupled to the multi-parameter monitor 32 (or other monitor 12) for patient monitoring, without requiring the operator to determine the unique, proper receptacle 26 for each type of connector 16 or for each type of sensor 14, for example.

In certain embodiments, the sensor 14 may not be directly coupled to the monitor 12 during a patient monitoring session, but rather, the sensor 12 may be configured to collect and store data in a memory of the sensor 14 during the patient monitoring session. In some embodiments, the sensor 14 may additionally include a processor configured to process the data, and thus, in certain circumstances, the sensor 14 may calculate and store physiological parameters. In such embodiments, the connector 16 may be used to couple the sensor 14 to the monitor 12 after the patient monitoring session to transfer the stored data or stored calculated parameters from the sensor 14 to the monitor 12. Additionally or alternatively, the connector 16 may be utilized to connect the sensor 14 to the monitor 12 before or after the patient monitoring session to provide or adjust programmed settings, provide instructions or operational parameters, download new software or programs to the sensor 12, or recharge a battery within the sensor 14, for example.

In some embodiments, the sensor 14 may be a wireless sensor 14 that is configured to wirelessly communicate with the monitor 12. Thus, the sensor 14 may wirelessly transmit either raw detector signals or calculated physiological parameter values to the monitor 12 via a wireless module. Additionally, the monitor 12 may use a wireless module to send the sensor 14 instructions and/or operational parameters, such as settings inputted by the operator using the monitor 12. The wireless modules may enable the monitor 12 and the sensor 14 to transmit and/or receive data wirelessly. In such embodiments, the connector 16 and the receptacle 26 may be utilized to connect the wireless sensor 14 to the monitor 12 as a backup method of data transfer. Additionally or alternatively, the connector 16 and the receptacle 26 may be utilized to couple the sensor 14 to the monitor 12 before or after a monitoring session to adjust programmed settings, download new software or programs to the sensor 14, ensure the correct monitor 12 is displaying data for the correct patient, and/or recharge a battery within the sensor 14, for example. Additionally or alternatively, the wireless functionality for the wireless sensor 14 may be provided in a separate wireless module, and the connector 16 may connect to a receptacle 26 on the wireless module.

In wireless configurations, the sensor 14 may also include a power source, such as a battery, and appropriate circuitry. Additionally, wireless modules of the sensor 14 and of the monitor 12 may be configured to communicate using the IEEE 802.15.4 standard, and may be, for example, ZigBee, WirelessHART, or MiWi modules. Additionally or alternatively, the wireless module may be configured to communicate using the Bluetooth standard, one or more of the IEEE 802.11 standards, an ultra-wideband (UWB) standard, or a near-field communication (NFC) standard. In such wireless configurations, it may be desirable for the connector 16 to be removably coupleable to the sensor 14, as the wireless sensor 14 is not generally physically connected to the monitor 12 during a patient monitoring session. In some cases, the connector 16 may be attached to the sensor 14 via a flexible connection, may extend directly from the sensor body 18, or may be integrated into the sensor body 18 to facilitate connecting the sensor 14 to the monitor 12 when wired communication is desired.

In embodiments where the sensor 14 is a pulse oximetry sensor 14A, the pulse oximetry sensor 14A may include one or more emitters 20 configured to transmit light. In addition, the pulse oximetry sensor 14A may include one or more detectors 22 to detect light transmitted from the emitters 20 into a patient's tissue after the light has passed through the blood perfused tissue. The detectors 22 may generate a photoelectrical signal correlative to the amount of light detected. The emitter 20 may be a light emitting diode (LED), a superluminescent light emitting diode, a laser diode or a vertical cavity surface emitting laser (VCSEL). Generally, the light passed through the tissue is selected to be of one or more wavelengths that are absorbed by the blood in an amount representative of the amount of the blood constituent present in the blood. The amount of light passed through the tissue varies in accordance with the changing amount of blood constituent and the related light absorption. For example, the light from the emitter 20 may be used to measure blood oxygen saturation, water fractions, hematocrit, or other physiological parameters of the patient.

In certain embodiments, the emitter 20 may include at least two LED's configured to emit at least two (e.g., red and infrared) wavelengths of light. The red wavelength may be between about 600 nanometers (nm) and about 700 nm, and the IR wavelength may be between about 800 nm and about 1000 nm. However, any appropriate wavelength (e.g., green, yellow, etc.) and/or any number of wavelengths (e.g., three or more) may be used. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure. Additionally, the pulse oximetry sensor 14A may also be configured to monitor various other physiological parameters, such as respiration rate, continuous non-invasive blood pressure (CNIBP), tissue water fraction, hematocrit, and/or water content. The pulse oximetry sensor 14A may include additional functionality, such as temperature or pressure sensing functionality, for example.

Figure 2:
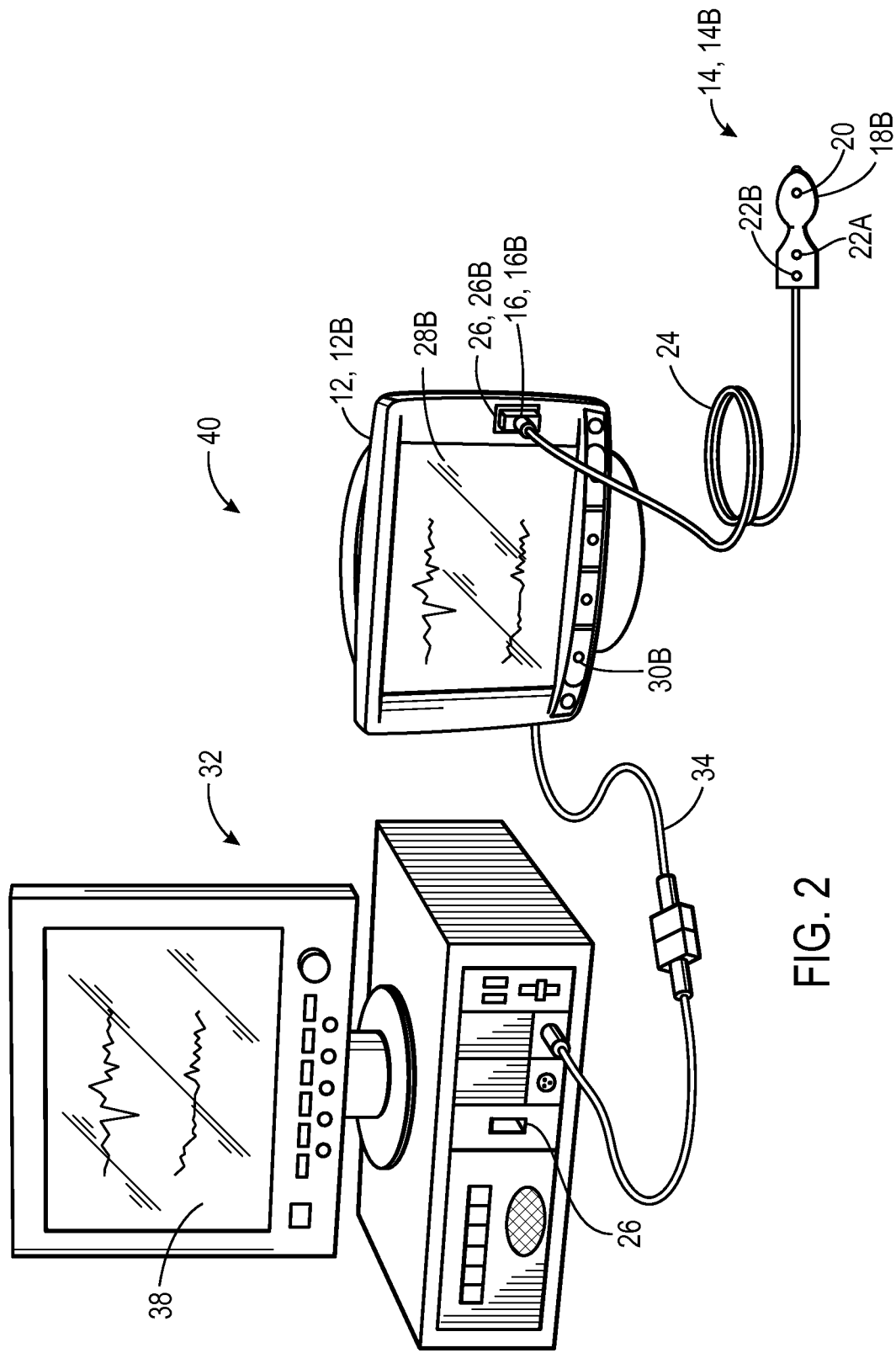
FIG. 2 is a front perspective view of an embodiment of a regional oxygen saturation monitoring system.

As discussed above, the multiple orientation connector 16 of the present disclosure may be adapted for use with a variety of sensors 14 and/or a variety of monitors 12. For example, as illustrated in FIG. 2, the connector 16 is a regional saturation connector 16B that is configured to couple a regional saturation sensor 14B to a regional saturation monitor 12B to form a regional saturation monitoring system 40. The regional saturation sensor 14B may have a sensor body 18B that supports various components (e.g., sensing components), such as emitters 20 and detectors 22. For example, the sensor body 18B may support one emitter 20 and two detectors 22 (e.g., a first detector 22A and a second detector 22B). The emitters 20 and detectors 22 may generally have the same light emitting and detecting properties as the emitters 20 and detectors 22 described above with respect to the pulse oximetry sensor 14A. However, different spacing between the emitter 20 and each of the detectors 22A, 22B enable the collection of oxygen saturation data for the particular region of the body beneath the regional saturation sensor 14B. Although the regional saturation sensor 14B may be configured to be applied to a forehead of the patient, the regional saturation sensor 14B may be configured for placement at any suitable body location.

As shown in FIG. 2, the connector 16B may extend from the sensor body 18B. The regional saturation monitor 12B may include the receptacle 26, which may be a regional saturation receptacle 26, to receive at least a portion of the connector 16 to electrically couple the regional saturation sensor 14B to the regional saturation monitor 12B. The regional saturation monitor 12B may be configured to process the signals received from the regional saturation sensor 12B via the connector 16. Additionally, the regional saturation monitor 12B may have a display 28B and inputs 30B. The regional saturation monitor 12B may also be coupled to a multi-parameter monitor 32, as described above with respect to FIG. 1. Additionally, the multi-parameter monitor 32 may have one or more receptacles 26 configured to receive the connector 16, and in such configurations, the regional saturation sensor 14B may be directly coupled to the multi-parameter monitor 32 via the connector 16. In certain embodiments, the multi-parameter monitor 32 may have some or all of the functionality of the regional saturation monitor 12B, as well as additional functionality.

Figure 3:
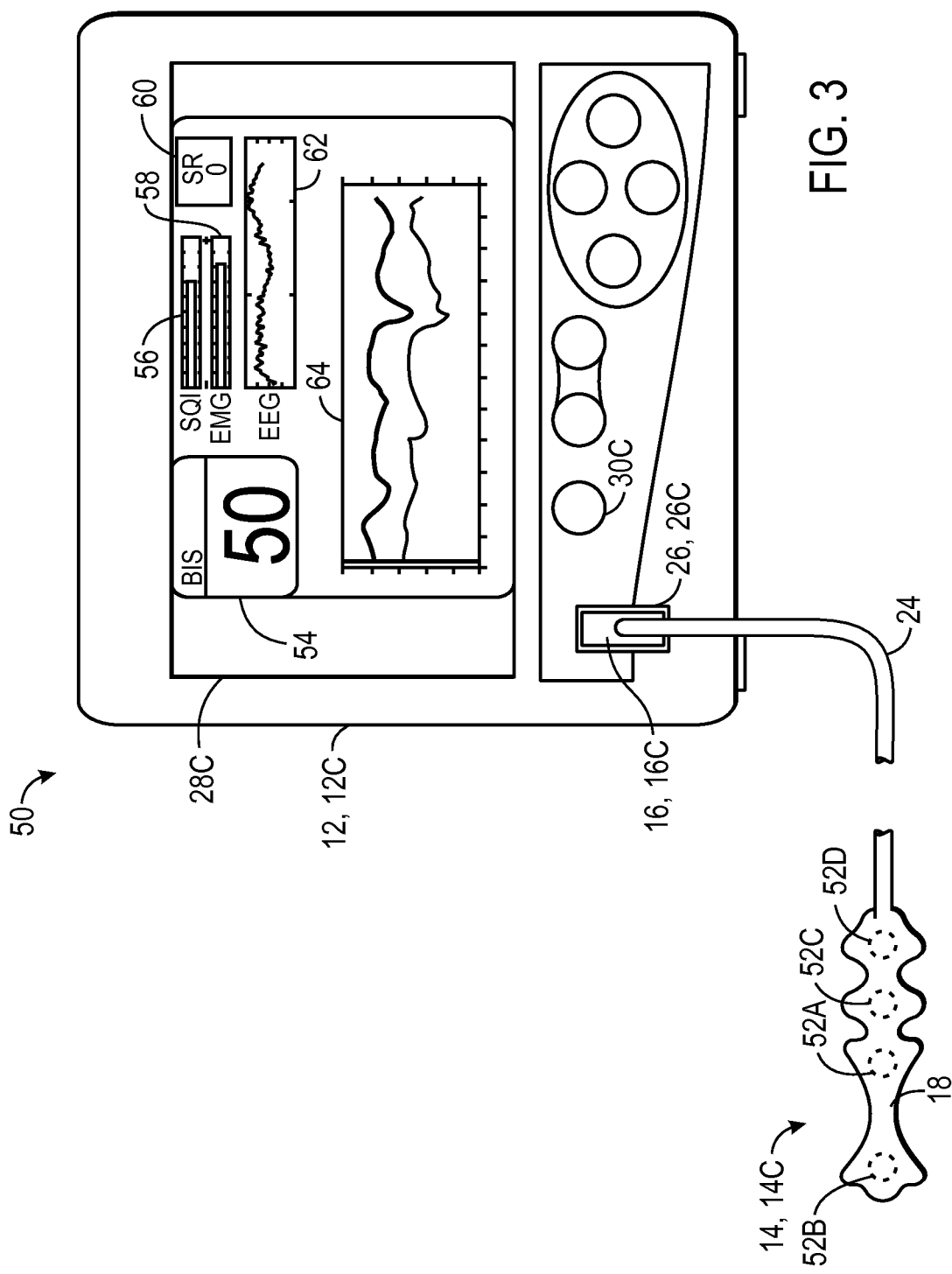
FIG. 3 is a front view of an embodiment of a bispectral index monitoring system.

Additionally, as shown in FIG. 3, the connector 16 may be an EEG connector 16C that is configured to couple an EEG sensor (e.g., a BIS™ sensor, Covidien LP, Boulder, Colo.) 14C to an EEG monitor 12C (e.g., a BIS™ monitor, Covidien LP, Boulder, Colo.) as part of an EEG monitoring system 50. The EEG sensor 14C may include one or more electrodes 52 for collecting an EEG signal. In certain embodiments, the EEG sensor 14C includes a sensing electrode 52a for detecting EEG signals, an artifact-monitoring electrode 52b for monitoring artifacts resulting from muscular movement (e.g., eye twitching), a grounding electrode 52c, and a reference electrode 52d. It should be noted that in certain embodiments, the sensor 12 may be capable of performing EEG measurements with fewer than four electrodes 52, or more than four electrodes 52. For example, in one embodiment, the sensor 12 may be capable of performing EEG measurements using only electrodes 52A, 52C, and 52D. In other embodiments, such as where the sensor 12 is a bilateral sensor, the electrodes 16 may include a reference electrode configured to be placed at the center of the patient's forehead, two electrodes each configured to be placed above an eye of the patient to monitor artifacts from eye twitching or movement, one ground electrode, and two electrodes each configured to be placed against the patient's temples for monitoring.

The EEG monitor 12C may be configured to algorithmically calculate physiologic informal from the EEG signal. As noted above, EEG is a measure of a patient's level of consciousness during general anesthesia. Examples of parameters assessed during the EEG monitoring may include the effects of anesthetics, evaluating asymmetric activity between the left and right hemispheres of the brain in order to detect cerebral ischemia, and detecting burst suppression. Such monitoring may be used to determine if the patient's anesthesia level is appropriate and to maintain a desired anesthesia depth.

As shown, the EEG sensor 14C may be electrically coupled to the EEG monitor 12C via the connector 16C. More specifically, the EEG monitor 12C may include the receptacle 26, which may be an EEG receptacle 26C, configured to receive at least a portion of the connector 16. The EEG monitor 14C may include a display 28c and inputs 30c. The display 28c may provide various types of information, such as an index value such as a patient's BIS value 54 (offered in BIS™ monitors from Covidien LP, Boulder, Colo.), which represents a dimensionless number (e.g., ranging from 0, i.e., silence, to 100, i.e., fully awake and alert) output from a multivariate discriminate analysis that quantifies the overall bispectral properties (e.g., frequency, power, and phase) of the EEG signal. The EEG monitor 12C may also display a signal quality index (SQI) bar graph 56 that indicates the signal quality of the EEG channel source(s), an electromyography (EMG) bar graph 58 that indicates the power (e.g., in decibels) in the frequency range of 70 to 110 Hz, and a suppression ratio (SR) 60 that represents the percentage of epochs over a given time period (e.g., the past 63 seconds) in which the EEG signal is considered suppressed (i.e., low activity). The EEG monitor 12C may also display the EEG waveform 62 and/or trends 64 over a certain time period (e.g., one hour) for EEG, SR, EMG, SQI, and/or other parameters.

Although not shown in FIG. 3, the EEG monitor 12C may also be coupled to a multi-parameter monitor 32, such as the multi-parameter monitor 32 described above with respect to FIGS. 1 and 2. Additionally, as described above, the multi-parameter monitor 32 may have the receptacle 26 that is configured to receive the connector 16, and in such configurations, the EEG sensor 14C may be directly coupled to the multi-parameter monitor 32 via the connector 16. The multi-parameter monitor 32 may be configured to receive signals and/or process signals or parameters received from the EEG sensor 14C. In certain embodiments, the multi-parameter monitor 32 may have some or all of the functionality of the EEG monitor 12C, as well as additional functionality.

FIGS. 1-3 illustrate various systems 10, 40, 50 that utilize multiple orientation connectors 16 to couple sensors 14 to monitors 12. The configuration of the connector 16 and/or receptacle 26 utilized for each type of system 10, 40, 50 may be unique or different (e.g., the pulse oximetry connector 16A, the regional saturation connector 16B, and the EEG connector 16C), or the connector 16 and corresponding receptacle 26 for each system may be the same. For example, the connector 16 may be configured to couple various types of sensors 14 (e.g., pulse oximetry sensors 14A, regional saturation sensors 14B, and/or EEG sensors 12C) to corresponding receptacles 26 of various types of monitors 12 (e.g., pulse oximetry monitors 12A, regional saturation monitors 12B, EEG monitors 12C, and/or multi-parameter monitors 32). Additionally, while examples of some types of sensors 14 and monitors 12, 32 are particularly described above, it should be understood that the connectors 16 may be used to electrically couple a wide variety of sensors 14 to a wide variety of monitors 12, 32.

Figure 4:
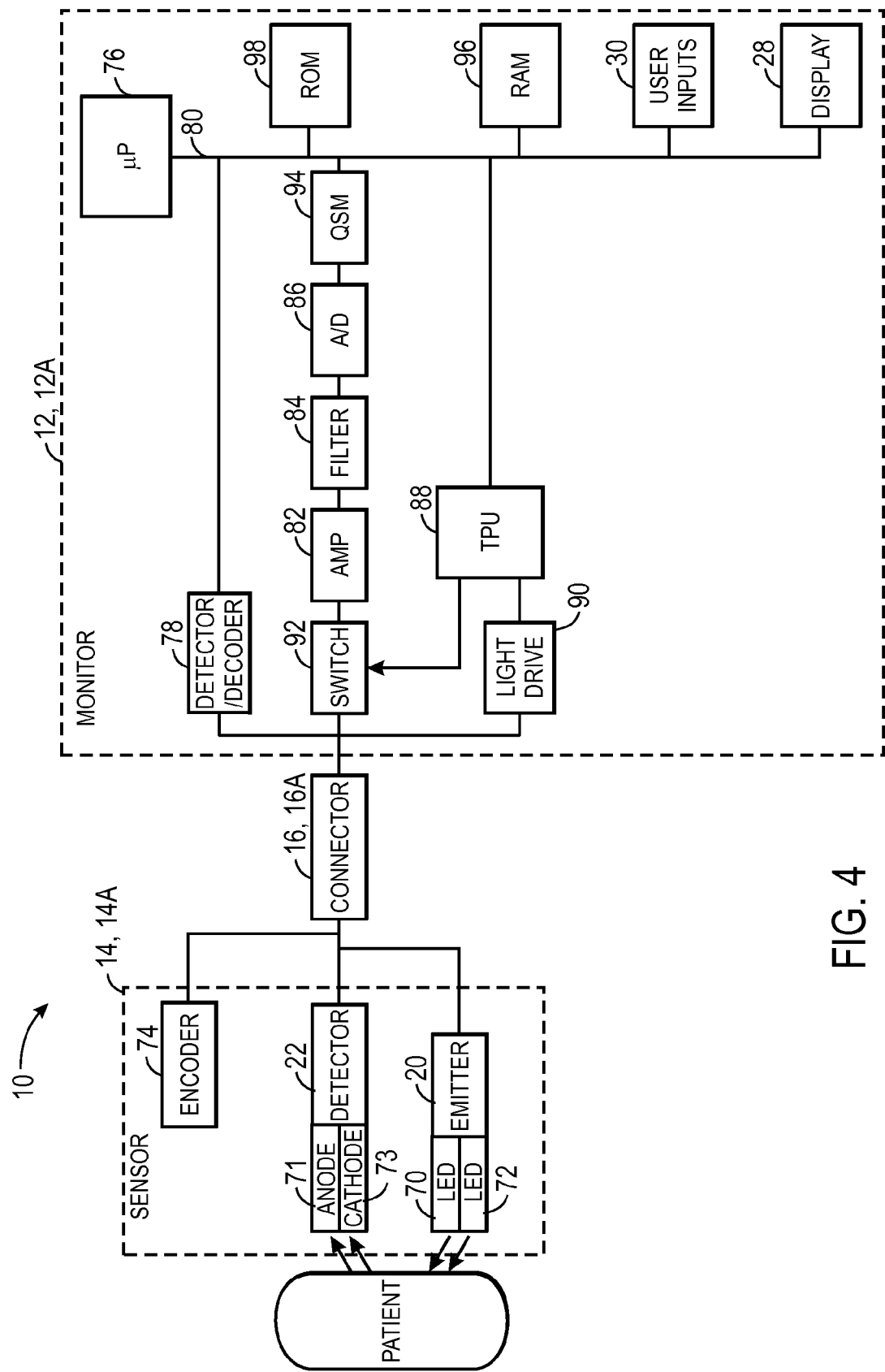
FIG. 4 is a block diagram of the pulse oximetry monitoring system of FIG. 1, in accordance with an embodiment.

FIG. 4 is a block diagram of the medical monitoring system 10 of FIG. 1, in accordance with an embodiment. As noted above, the connector 16 is configured to mechanically and electrically couple the sensor 14 to the monitor 12. The connector 16 may be inserted into the receptacle 26 in multiple different orientations (e.g., two, three, four, five, six, or more orientations). In some such cases, the monitor 12 may be configured to determine the orientation of the connector 16 relative to the receptacle 26 of the monitor 12. As discussed in more detail below, such a determination may enable the monitor 12 to remap or to adjust electrical contacts of the receptacle 26 to facilitate communication between the monitor 12 and the sensor 14, regardless of the orientation of the connector 16 with respect to the receptacle 26 of the monitor 14.

As shown, the sensor 14 includes the emitter 20 and the detector 22. In the illustrated embodiment, the emitter 20 includes a first LED 70 configured to emit a first wavelength of light and a second LED 72 configured to emit a second wavelength of light. The detector 22 includes an anode 71 and a cathode 73. The sensor 14 also includes an encoder 74, which may contain information about the sensor 14, such as what type of sensor it is (e.g., a type of sensor 14, a location where the sensor 14 is to be placed, etc.) and/or how the sensor 14 is to be driven (e.g., a wavelength of light emitted by the emitter 20). The encoder 74 may also contain information related to a configuration of pins of the connector 16 that is coupled to the sensor 14, which may in turn facilitate an appropriate exchange of signals between the monitor 12 and the sensor 14, as discussed in more detail below. This information may also allow the monitor 12 to select appropriate algorithms and/or calibration coefficients and/or to derive a filter for estimating the patient's physiological characteristics.

The encoder 74 may, for instance, be a memory on which information may be stored for communication to the monitor 12. The encoder 74 may store information related to the wavelength of the emitter 20. The encoder 74 may, for instance, be a coded resistor, EEPROM or other coding devices (such as a capacitor, inductor, PROM, RFID, parallel resident currents, or a colorimetric indicator) that may provide a signal to a microprocessor 76 or other processing circuitry of the monitor 12 related to the characteristics of the sensor 14 to enable the microprocessor 76 to determine the appropriate calibration characteristics. As discussed in more detail below, the monitor 12 may interact (e.g., transmit, receive, or exchange electrical signals) with the encoder 74 to determine the orientation of the connector 16 relative to the receptacle 26 of the monitor 12. In some embodiments, the data or signal from the encoder 74 may be decoded by a detector/decoder 78 in the monitor 12. In some embodiments, the encoder 74 and/or the decoder 78 may not be present. Although shown in the sensor 14, the encoder 74 may be provided in the connector 16 or in the cable 24, for example.

The microprocessor 76 of the monitor 12 may be coupled to an internal bus 80. The received signal from the sensor 14 may be passed through an amplifier 82, a low pass or bandpass filter 84, and an analog-to-digital converter 86. A time processing unit (TPU) 88 may provide timing control signals to light drive circuitry 90, which controls when the optical components of the optical sensor (e.g., sensor 14) is activated, and, if multiple light sources are used, the multiplexed timing for the different light sources. TPU 90 may also control the gating-in of signals from the sensor 14 through a switching circuit 92. These signals are sampled at the proper time, depending at least in part upon which of multiple light sources is activated, if multiple light sources are used. The digital data may then be stored in a queued serial module (QSM) 94, for later downloading to RAM 96 or ROM 98 as QSM 94 fills up. In addition, the monitor 12 may include the display 28 and control inputs 30, such as knobs, switches, keys and keypads, touchscreens, buttons, etc., to provide for operation and configuration of the monitor 12.

As discussed in more detail below, the circuitry (e.g., the microprocessor 76) of the monitor 12 may be configured to determine the orientation of the connector 16 relative to the receptacle 26 of the monitor 12 based at least in part on electrical signals exchanged between the monitor 12 and one or both of the connector 16 and the sensor 12. As discussed in more detail below, the monitor 12 may be configured to interact with one or more of the encoder 74, the emitter 20, or the detector 22 to determine the orientation of the connector 16 relative to the receptacle 26 of the monitor 12. For example, the monitor 12 may read the encoder 74, measure a voltage drop across the first LED 70 and/or the second LED 72 of the emitter 20, and/or pass a current through the detector 22 to determine the orientation of the connector 16 relative to the receptacle 26 of the monitor 12. Additionally or alternatively, as discussed in more detail below, the monitor 12 may be configured to measure crosstalk between pins of the connector 16 and/or interact with an orientation element of the connector 16 to determine the orientation of the connector 16 relative to the receptacle 26 of the monitor 14.

After the orientation of the connector 16 is determined, the monitor 12 may be configured to use the orientation to appropriately drive the emitter 20 of the sensor 12, to receive and interpret signals from the detector 22, and/or to determine various physiological characteristics, using the microprocessor 76. For example, the monitor 14 may be configured to determine blood pressure, oxygen saturation, heart rate, and/or other physiological parameters using one or more algorithms. The algorithms may employ certain coefficients, which may be empirically determined, and may correspond to the wavelengths of light used. The algorithms and coefficients may be stored in a ROM 98 or other suitable computer-readable storage medium or memory circuitry and accessed and operated according to microprocessor 76 instructions.

As discussed above, one or more functions of the monitor 12 may also be implemented directly in the sensor 12 and/or the connector 16. For example, in some embodiments, the sensor 14 may include one or more processing components configured to calculate the blood pressure, the oxygen saturation, and/or various physiological parameters from the signals obtained from the patient. The sensor 14 and/or the connector 16 may have varying levels of processing power. For example, in some embodiments, the data output to the monitor 12 may be analog signals, such as detected light signals (e.g., pulse oximetry signals or regional saturation signals), or processed data.

Although FIG. 4 illustrates certain processing components of the monitor 12 in the context of the pulse oximetry system 10, it should be understood that similar processing components and/or features may be provided in the regional saturation system 40 and/or the EEG system 50. For example, the regional saturation system 40 may include the regional saturation sensor 14B having multiple emitters 20 and/or multiple detectors 22. The regional saturation monitor 14B may include the microprocessor 76 that is configured to determine the orientation of the connector 16 in the manner set forth above. The regional saturation monitor 12B may also be configured to use the orientation to properly drive the emitter 20 of the sensor 14B, to receive and interpret signals from the detectors 22, and/or to determine various physiological characteristics, using the microprocessor 76. Similarly, the EEG monitor 12C may include the microprocessor 76 that is configured to determine the orientation of the connector 16 in the manner set forth above. The EEG monitor 12C may also be configured to use the orientation to properly exchange signals with the electrodes 52 of the sensor 14C, to receive and interpret signals from the electrodes 52, and/or to determine various physiological characteristics, using the microprocessor 76.

Figure 5:
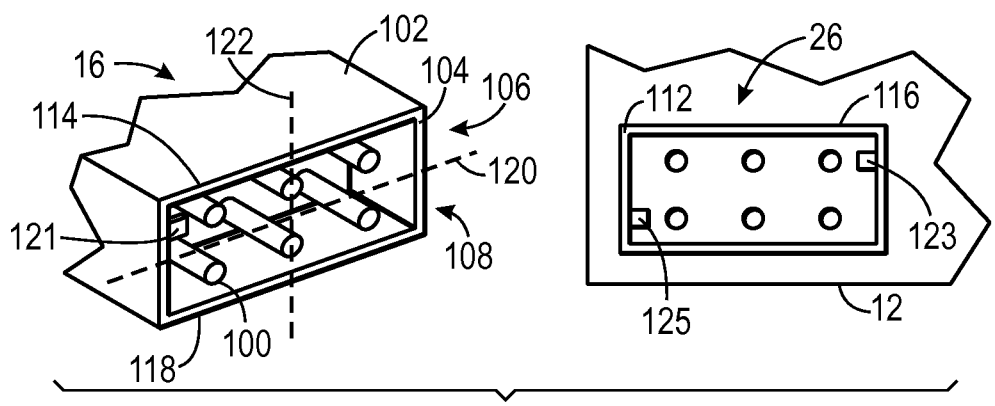
FIG. 5 is a perspective view of an embodiment of a portion of a multiple orientation connector and a portion of a receptacle of a monitor.

FIG. 5 is a perspective view of an embodiment of the connector 16 and the receptacle 26. The connector 16 includes electrical contacts 100 (e.g., pins) positioned within a housing 102 (e.g., a rectangular housing). The pins 100 may be recessed relative to a front face 104 of the housing 102 to protect the pins 100 during handling of the connector 16, for example. In the illustrated embodiment, the pins 100 are arranged in two rows, a first row 106 and a second row 108, although any number (e.g., 1, 2, 3, 4, 5, or more) rows of pins 100 may be provided. Additionally, as shown, three pins 100 are positioned in each of the first row 106 and the second row 108, although each row may have any suitable number of pins 100 (e.g., 2, 3, 4, 5, 6, or more). Furthermore, although the housing 102 is rectangular in FIG. 5, in various embodiments, the housing 102 may have any suitable shape, such as square, hexagonal, octagonal, or the like, that enables insertion of the connector 16 into the receptacle 26 in more than one orientation.

To accomplish this multiple orientation functionality, in an embodiment, the shape of the connector housing 102 is symmetric, such that the connector housing 102 has the same outer profile when rotated by 180 degrees. In an embodiment, the shape of the connector housing 102 is symmetric about more than one axis, such that the connector housing 102 has the same outer profile when rotated by other amounts, such as 45 degrees, 90 degrees, etc. In an embodiment, the connector housing 102 is shaped such that it has two or more symmetric orientations. In a further embodiment, the connector housing 102 is shaped such that it has two or more discrete, symmetric orientations. For example, a circular connector housing 102 provides a continuous range of symmetric orientations, while an oval connector housing 102 provides two discrete symmetric orientations. Providing discrete housing orientations is useful so that the pins 100 inside the connector 16 are automatically aligned when the connector housing 102 is aligned. Alternatively, a circular housing may be used with an orientation element, as described below, to facilitate proper orientation of the connector 16 into the receptacle 26. In each embodiment, the receptacle 26 is shaped to mate with the connector housing 102. The receptacle 26 and the connector 16 meet at a matching, symmetric interface, providing the ability to connect them together in at least two different orientations.

In the illustrated embodiment, the receptacle 26 includes electrical contacts 110 (e.g., sockets) configured to mechanically and electrically interface with (e.g., receive) the pins 100. When the connector 16 is properly inserted into the receptacle 26, each one of the pins 100 is electrically coupled to one corresponding socket 110. As shown, the receptacle 26 includes a recess 112 configured to receive a portion of the housing 102 of the connector 16 to facilitate a secure fit between the connector 16 and the receptacle 26, for example.

In the illustrated embodiment, the connector 16 has 180 degree symmetry, enabling the connector 16 to be coupled to the receptacle 26 in either one of two different orientations. For example, a first side 114 of the connector 16 may be adjacent to a top edge 116 of the receptacle 26 in a first orientation of the connector 16 relative to the receptacle 26, while a second side 118 of the connector 16 may be adjacent to the top edge 116 of the receptacle 26 in a second orientation of the connector 16 relative to the receptacle 26. To facilitate the reversibility of the connector 16, the pins 100 and/or the housing 102 of the connector 16 may have a configuration that is symmetrical relative to a horizontal axis 120 and relative to a vertical axis 122 of the connector 16. The pins 100 may be centered relative to sides of the housing 102 and/or spaced evenly from one another, and the receptacle 26 has a corresponding symmetrical configuration. The connector 16 may have a locking mechanism to prevent accidental disconnection (e.g., up to a certain amount of pull force), which may be designed so it can connect in more than one orientation, for example by having a ridge on either side (e.g., one or both of which go under a corresponding tab on the connector 16).

As shown, the connector 16 includes an orientation element 121 that is configured to facilitate determination of the orientation in which the connector 16 is inserted into the receptacle 26. The orientation element 121 may have any suitable form and may be disposed in any suitable position on the connector 16. The receptacle 26 may include one or more features to enable detection of the orientation element 121. For example, as shown, the receptacle 26 includes two detection elements 123, 125 that may detect the orientation element 121 via mechanical contact or via optical or electrical techniques. Detection of the orientation element 121 may, in turn, enable determination of the orientation of the connector 16 relative to the receptacle 26, as discussed in more detail below. In certain embodiments, the orientation element 121 may be configured to facilitate proper insertion of the connector 16 into the receptacle 26 of a system (e.g., a legacy monitor) that is unable to determine the orientation of the connector 16.

Figure 6:
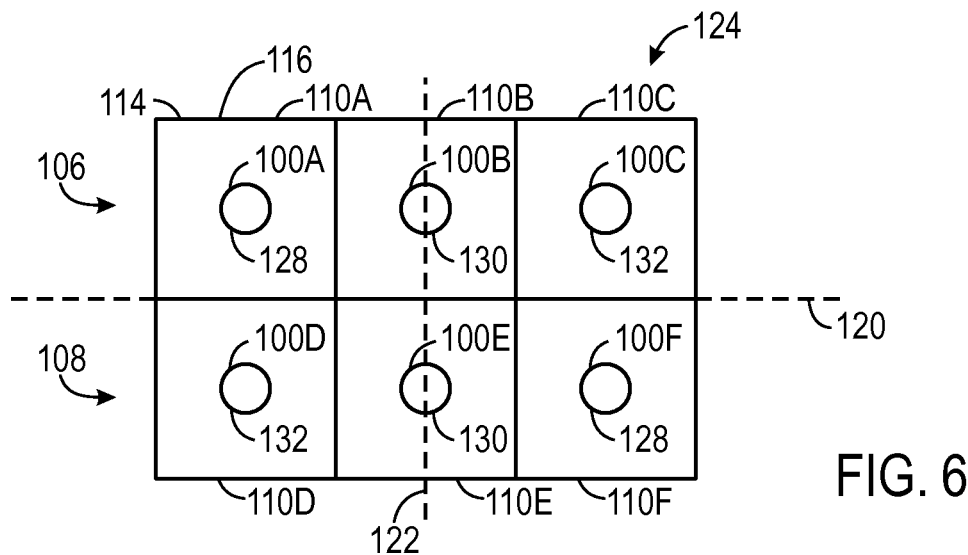
FIG. 6 is a schematic diagram of a multiple orientation connector having a two-dimensional array of six pins inserted within a receptacle of a monitor in a first orientation, in accordance with an embodiment.
Figure 7:
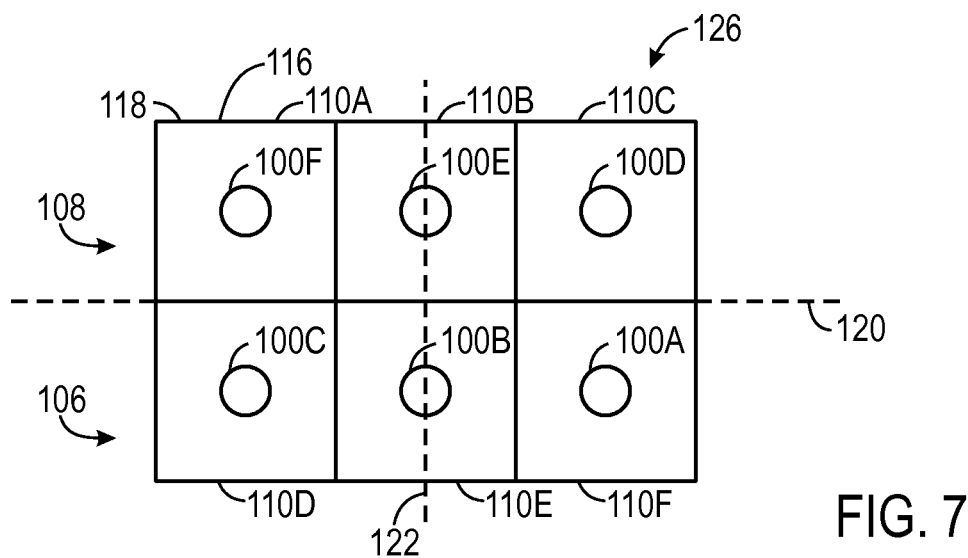
FIG. 7 is a schematic diagram of the multiple orientation connector of FIG. 6 inserted within the receptacle of the monitor in a second orientation, in accordance with an embodiment.

FIG. 6 is a schematic diagram of the connector 16 having a two-dimensional array of six pins 100 inserted within the sockets 110 of the receptacle 26 of the monitor 12 in a first orientation 124. In the first orientation 124, the first side 114 of the connector 16 is adjacent to the top edge 116 of the receptacle 26. FIG. 7 is a schematic diagram of the connector 16 of FIG. 6 inserted within the sockets 110 of the receptacle 26 of the monitor 12 in a second orientation 126. In the second orientation 126, the second side 118 of the connector 16 is adjacent to the top edge 116 of the receptacle 26. In the illustrated embodiment, the pins 100 are arranged in two rows, the first row 106 and the second row 108, and three pins 100 are positioned in each of the first row 106 and the second row 108. As shown in FIGS. 6 and 7, when the connector 16 is properly inserted into the receptacle 26, each of the pins 100 aligns with and is electrically coupled to one of the sockets 110 regardless of whether the connector 16 is in the first orientation 124 or the second orientation 126.

When the connector 16 is inserted into the receptacle 26 in the first orientation 124 shown in FIG. 6, a first pin 100A is coupled to a first socket 110A, a second pin 100B is coupled to a second socket 110B, a third pin 100C is coupled to a third socket 110C, a fourth pin 100D is coupled to a fourth socket 110D, a fifth pin 100E is coupled to a fifth socket 110E, and a sixth pin 100F is coupled to a sixth socket 110F. When the connector 16 is inserted into the receptacle 26 in the second orientation 126 shown in FIG. 7, the first pin 100A is coupled to the sixth socket 110F, the second pin 100B is coupled to the fifth socket 110E, the third pin 100C is coupled to the fourth socket 110D, the fourth pin 100D is coupled to the third socket 110C, the fifth pin 100E is coupled to the second socket 110B, and the sixth pin 100F is coupled to the first socket 110A. Thus, regardless of whether the connector 16 is inserted into the receptacle 26 in the first orientation 124 or the second orientation 126, the pins 100 are electrically coupled to the sockets 110 of the receptacle 26.

The pins 100 may be assigned (e.g., coupled) to various components of the sensor 14. The connector 16 for use with the pulse oximetry sensor 14A may have at least four pins 100 (e.g., four, five, six, or more). For example, when the connector 16 is used with the pulse oximetry sensor 14A, the first LED 70 and the second LED 72 may be arranged in a back-to-back (e.g., cross-coupled) configuration and two pins 100 may each be coupled to the first LED 70 and to the second LED 72 to transmit light drive signals from the monitor 12 to the LED's 70, 72 of the emitter 20. In other embodiments, the LED's 70, 72 may not be cross-coupled, and one pin 100 may be coupled to an anode of the first LED 70 and another pin 100 may be coupled to an anode of the second LED 72 to transmit light drive signals from the monitor 12 to the LED's 70, 72 of the emitter 20. In such cases, another pin 100 may be coupled to a common cathode for the LED's 70, 72, or one pin 100 may be coupled to a cathode of the first LED 70 and another pin 100 may be coupled to a cathode of the second LED 72. Additionally, one pin 100 may be coupled to the anode 71 of the detector 22 and another pin 100 may be coupled to the cathode 73 of the detector 22 to receive and transmit signals from the photodetector 22. Additionally, as noted above, the pulse oximetry sensor 14A may also include the encoder 74, and in such cases, one or more pins 100 of the connector 16 may be coupled to the encoder 74. One or more additional pins 100 in the connector 16 may have any suitable function. For example, one or more additional pins 100 may be grounded (e.g., a ground pin) or may provide shielding (e.g., a shield pin).

The pins 100 may be assigned in any of a variety of suitable manners. In certain embodiments, a subset of the pins 100 may be assigned to form a functional group (e.g., a functional pair) having 180 degree symmetry. The pins 100 of each functional pair may be symmetrical relative to one another about the horizontal center line 120 and the vertical center line 122 (e.g., have 180 degree symmetry). Furthermore, one pin 100 of each functional pair may be positioned in the first row 106, while another pin 100 of each functional pair may be positioned in the second row 108. For example, as shown, in one embodiment having six pins 100, the first pin 100A and the sixth pin 100F may form the first functional pair 128, the second pin 100B and the fifth pin 100E may form the second functional pair 130, and the third pin 100C and the fourth pin 100D may form the third functional pair 132.

Thus, the connector 16 may include the connector housing 102 that has a plurality of discrete, symmetric orientations, and an interface having a plurality of pins 100 arrange in symmetric functional pairs. Each functional pair may include pins 100 having similar functions and/or pins 100 configured to transmit similar signals. For example, the pins 100 that are coupled to the anode 71 and the cathode 73 of the detector 22 may form one functional pair, such as the first functional pair 128. Additionally, the pins 100 that are coupled to the first LED 70 and the second LED 72 may form one functional pair, such as the second functional pair 130. The pin 100 that is coupled to the encoder 74 and the ground pin 100 may form one functional pair, such as the third functional pair 132, as the encoder 74 may transmit information to the monitor 12 at the beginning of a monitoring session and then be grounded, for example.

In embodiments having the pins 100 arranged in functional pairs, the corresponding socket 110 of the receptacle 26 may be configured to contact one of the pins 100 of a particular functional pair regardless of the orientation of the connector 16. In other words, such a configuration may enable the sockets 110 of the receptacle 26 to have designated or limited purposes or functions, even while accommodating multiple orientations of the connector 16. For example, two sockets 110 (e.g., the second socket 110B and the fifth socket 110E, as shown in FIGS. 6 and 7) may be LED sockets 110 and may be in contact with the two pins 100 (e.g., the second pin 100B and the fifth pin 100E as shown in FIGS. 6 and 7) that are coupled to the first LED 70 and the second LED 72 regardless of the orientation of the connector 16.

By way of another example, in certain embodiments, the first pin 100A may be coupled to the cathode 73 of the detector 22 and the sixth pin 100F may be coupled to the anode 71 of the detector 22, and the first pin 100A and the sixth pin 100F may form the first functional pair 128. In such cases, the first socket 110A and the sixth socket 110F of the receptacle 26 may be detector sockets 110 dedicated to receiving signals from the detector 22 of the sensor 14. Circuitry (e.g., the microprocessor 76 of the monitor 12) of the monitor 12 may be configured to receive the detector 22 signals via the first socket 110A and the sixth socket 110F. Further, in some such cases, the circuitry may be configured to process the received signals based on a determined orientation of the connector 16, as discussed in more detail below. Such configurations may facilitate efficient exchange of signals between the connector 16 and the monitor 12, regardless of the orientation of the connector 16.

The examples provided above are not intended to be limiting, and it should be understood that the pins 100 may be arranged in any suitable manner that enables the connector 16 to be coupled to the receptacle 26 in multiple different orientations. For example, in some embodiments, the pins 100 that are coupled to the first LED 70 and the second LED 72 may be positioned remotely (e.g., separated by one or more pins 100 or on opposite lateral sides of the connector 16) from the pins 100 that are coupled to the anode 71 and the cathode 73 of the detector 22. In some embodiments, the pins 100 that are coupled to the encoder 74 and/or the ground pin 100 or shield pin 100 may be positioned between the pins 100 that are coupled to the LED's 70, 72 and the pins 100 that are coupled to the anode 71 and the cathode 73 of the detector 22. By way of further example, with reference to FIG. 6, the first pin 100A may be coupled to the first and/or second LED 70, 72, the fourth pin 100D may be coupled to either the first and/or second LED 70, 72, the third pin 100C may be coupled to either the anode 71 or the cathode 73 of the detector 22, and the sixth pin 100F may be coupled to either the anode 71 or the cathode 73 of the detector 22. In such cases, one or both of the second pin 100B or the fifth pin 100E may be coupled to the encoder 74 or may be the ground pin 100 or the shield pin 100. Such configurations may minimize interference, for example.

Additionally, in some embodiments, some or all of the sockets 110 of the monitor 12 may be configured to have more than one possible function, which can be determined at runtime by configuring a port multiplexor in firmware. For example, a certain socket 110 could be a digital-to-analog converter (DAC), an analog-to-digital converter (ADC), a digital socket, and/or a one-wire or serial peripheral interface (SPI) or inter-integrated circuit (I2C) interface for reading the encoder 74. If a certain type of calibration element (e.g., an R-Cal resistor) is coupled to the socket 110, a voltage drop may be measured using the ADC. If that same socket 110 is connected to the encoder 74, any of a variety of digital interfaces may be used to read it.

The six pin 100 connector 16 of FIGS. 6 and 7 may be suitable for use within the pulse oximetry system 10. In some cases, the six pin 100 connector 16 may be used with other types of systems, such as the regional saturation system 40 or the EEG system 50. However, as discussed above, the regional saturation sensor 14B of the regional saturation system 40 includes additional emitters 20 and/or detectors 22. Thus, it may be desirable for the connector 16 for use with the regional saturation sensor 14B to include more than six pins 100 (e.g., seven, eight, nine, ten, eleven, twelve, or more pins 100). Furthermore, certain medical monitoring systems, such as pulse oximetry systems 10 and regional saturation systems 40, include various elements that are often wired in pairs. For example, emitters 20 and detectors 22 are often wired in pairs and thus may benefit from a symmetrical arrangement of pins 100.

Figure 8:
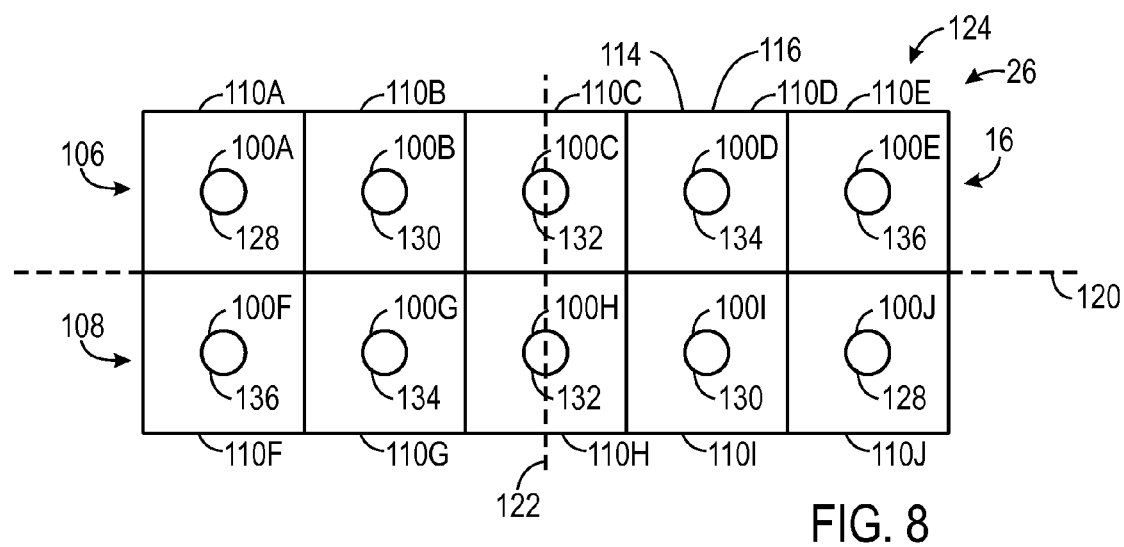
FIG. 8 is a schematic diagram of a multiple orientation connector having a two-dimensional array of ten pins inserted within a receptacle of a monitor in a first orientation, in accordance with an embodiment.
Figure 9:
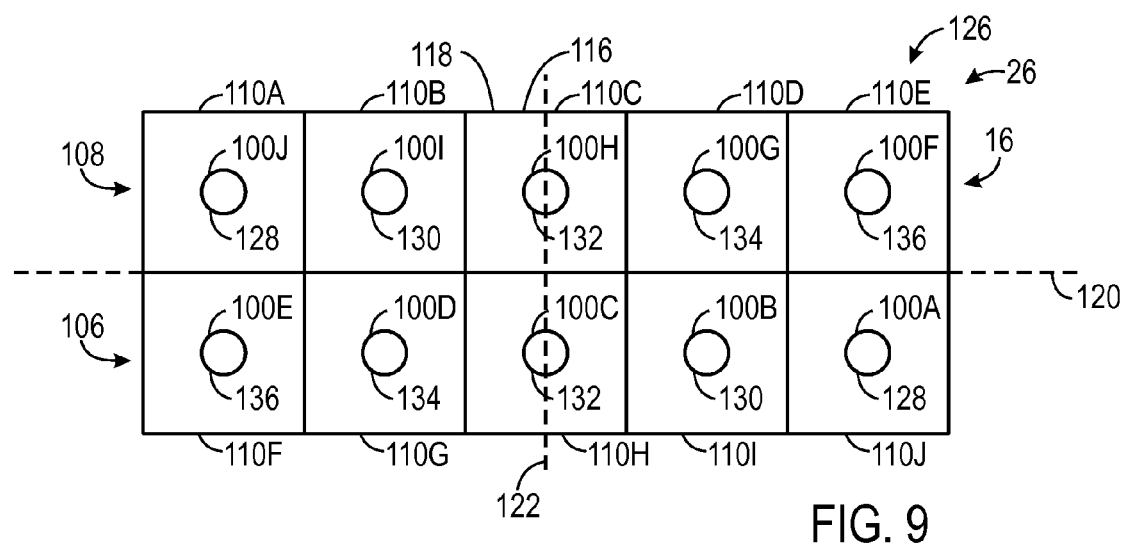
FIG. 9 is a schematic diagram of the multiple orientation connector of FIG. 8 inserted within the receptacle of the monitor in a second orientation, in accordance with an embodiment.

With the foregoing in mind, FIG. 8 is a schematic diagram of the connector 16 having a two-dimensional array of ten pins 100 inserted within the sockets 110 of the receptacle 26 of the monitor 12 in a first orientation 124. In the first orientation 124, the first side 114 of the connector 16 is adjacent to the top edge 116 of the receptacle 26. FIG. 9 is a schematic diagram of the connector of FIG. 8 inserted within the sockets 110 of the receptacle 26 of the monitor 12 in a second orientation 126. In the second orientation 126, the second side 118 of the connector 16 is adjacent to the top edge 116 of the receptacle 26. In the illustrated embodiment, the pins 100 are arranged in two rows, the first row 106 and the second row 108, and five pins 100 are positioned in each of the first row 106 and the second row 108. When the connector 16 is properly inserted into the receptacle 26, each of the pins 100 aligns with and is electrically coupled to one of the sockets 110 regardless of whether the connector 16 is in the first orientation 124 or the second orientation 126.

In the illustrated configuration, when the connector 16 is inserted into the receptacle 26 in the first orientation 124 shown in FIG. 8, a first pin 100A is coupled to a first socket 110A, a second pin 100B is coupled to a second socket 110B, a third pin 100C is coupled to a third socket 110C, a fourth pin 100D is coupled to a fourth socket 110D, a fifth pin 100E is coupled to a fifth socket 110E, a sixth pin 100F is coupled to a sixth socket 110F, a seventh pin 100G is coupled to a seventh socket 110G, an eighth pin 100H is coupled to an eighth socket 110H, a ninth pin 100J is coupled to a ninth socket 110J, and a tenth pin 100I is coupled to tenth socket 110I. When the connector 16 is inserted into the receptacle 26 in the second orientation 126 shown in FIG. 9, the first pin 100A is coupled to the tenth socket 110J, the second pin 100B is coupled to the ninth socket 110J, the third pin 100C is coupled to the eighth socket 110H, the fourth pin 100D is coupled to the seventh socket 110G, the fifth pin 100E is coupled to the sixth socket 110F, and the sixth pin 100F is coupled to the fifth socket 110E, the seventh pin 100G is coupled to the fourth socket 110D, the eighth pin 100H is coupled to the third socket 110C, the ninth pin 100J is coupled to the second socket 110B, and the tenth pin 100I is coupled to the first socket 110A. Thus, regardless of whether the connector 16 is inserted into the receptacle 26 in the first orientation 124 or the second orientation 126, the pins 100 are electrically coupled to the sockets 110 of the receptacle 26.

As discussed above, the pins 100 may be coupled to various components of the sensor 14. In the illustrated embodiment, when used with the regional saturation sensor 14B, one pin 100 may be coupled to the first LED 70 and/or to the second LED 72 and one pin 100 may be coupled to the first LED 70 and/or to the second LED 72 of the emitter 20. One pin 100 may be coupled to the anode 71 of a first one of the plurality of detectors 22 (e.g., the first detector 22A), and one pin 100 may be coupled to the cathode 73 of the first one of the plurality of detectors 22. One pin 100 may be coupled to the anode of a second one of the plurality of detectors 22 (e.g., the second detector 22B), and one pin may be coupled to the cathode 73 of the second one of the plurality of detectors 22. Additionally, one or more pins 100 may be coupled to the encoder 74, one or more pins 100 may be coupled to additional calibration or data elements (e.g., resistors or additional encoders 74), one or more pins 100 may be grounded, and/or one or more pins 100 may provide shielding, as set forth below.

More particularly, in certain embodiments, when used with the regional saturation sensor 14B, the first pin 100A may correspond to the cathode 73 of the first detector 22A, the second pin 100B may provide a shield, the third pin 100C may correspond to the first LED 70 and/or the second LED 72 of the emitter 20, the fourth pin 100D may correspond to the encoder 74, the fifth pin 100E may correspond to the cathode 73 of the second detector 22B, the sixth pin 100F may correspond to the anode 71 of the second detector 22B, the seventh pin 100G may correspond to the ground pin, the eighth pin 100H may correspond to the first LED 70 and/or the second LED 72, the ninth pin 100I may provide a shield, and the tenth pin 100J may correspond to the anode 71 of the first detector 22A.

Furthermore, the pins 100 may be assigned in any of a variety of suitable manners. In some cases, the pins 100 may be arranged into one or more functional pairs having 180 degree symmetry, as discussed above. For example, as shown in FIG. 8, in one embodiment having ten pins 100, the first pin 100A and the tenth pin 100J may form the first functional pair 128, the second pin 100B and the ninth pin 100I may form the second functional pair 130, the third pin 100C and the eighth pin 100H may form the third functional pair 132, the fourth pin 100D and the seventh pin 100G may form the fourth functional pair 134, and the fifth pin 100E and the sixth pin 100F may form the fifth functional pair 136. As noted above, each functional pair may include pins 100 having similar functions and/or pins 100 configured to transmit similar signals. For example, the pins 100 that are coupled to the anode 71 and the cathode 73 of the first detector 22A may form one functional pair, such as the first functional pair 128. The pins 100 that are coupled to the anode 71 and the cathode 73 of the second detector 22B may form one functional pair, such as the fifth functional pair 136. Additionally, the pins 100 that are coupled to the first LED 70 and the second LED 72 may form one functional pair, such as the third functional pair 132. The pin 100 that is coupled to the encoder 74 and the ground pin 100 may form one functional pair, such as the fourth functional pair 134, as the encoder 74 may transmit information to the monitor 12 at the beginning of a monitoring session and then be grounded, for example. In certain embodiments, two shield pins 100 may form one functional pair, such as the second functional pair 130, for example. As noted above, positioning the pins 100 of the functional pairs to have 180 degree symmetry may facilitate the exchange of signals between the connector 16 and the receptacle 26 and reduce software and/or hardware adjustments, as discussed in more detail below.

As noted above, in some embodiments, the connector 16 may be configured for use with multiple different types of sensors 14. For example, the connector 16 illustrated in FIG. 8 may be configured for use with the pulse oximetry sensor 14A and/or the regional saturation sensor 14B. Such connectors 16 may provide convenience in the medical setting because the uniform external appearance and configuration of the connectors may make the connectors relatively easy to recognize and operate in medical environments, for example. However, certain sensors 14 may utilize more pins 100 than other types of sensors 14. For example, the regional saturation sensor 14B includes additional emitters 20 and/or additional detectors 22 as compared with the pulse oximetry sensor 14A, and thus, the regional saturation sensor 14B may utilize more pins 100. Thus, when used with the pulse oximetry system 10, the connector 16 may have more pins 100 than needed for communicating with the monitor 12. Such configurations may enable additional shielding and/or functionality within the pulse oximetry monitoring system 10, for example. In other cases, certain pins 100 may be spare pins that are not utilized when the connector 16 is coupled to the pulse oximetry sensor 14A. For example, rather than including pins 100 for the additional information element and/or shielding, the connector 16 may include spare pins 100 that are not utilized when the connector 16 is coupled to the pulse oximetry sensor 14A.

As noted above, the pins 100 may be assigned in any of a variety of manners. When used with the pulse oximetry sensor 14A, the pins 100 of the connector 16 shown in FIG. 8 may have a similar arrangement or a different arrangement than when the connector 16 is used with the regional saturation sensor 14B. In one possible arrangement for use with the pulse oximetry sensor 14A, the anode 71 and the cathode 73 of the detector 22 form one functional pair, such as the first functional pair 128, the LED's 70, 72 form one functional pair, such as the third functional pair 132, and the encoder 74 and a ground pin 100 form one functional pair, such as the fourth functional pair 134. In some cases, two shield pins form one functional pair, such as the second functional pair 130. Furthermore, in some cases, one or more pins 100 may be coupled to one or more additional information elements, such as a resistor, and may form one functional pair, such as the fifth functional pair 136.

More particularly, when used with the pulse oximetry sensor 14A, the first pin 100A may correspond to the cathode 73 of the detector 22, the second pin 100B may be the shield pin 100, the third pin 100C may correspond to the first LED 70 and/or the second LED 72 of the emitter 20, the fourth pin 100D may correspond to the encoder 74, the fifth pin 100E and/or the sixth pin 100F may be an additional shield pin 100, a spare pin, or may correspond to an additional calibration or information element of the sensor 14 (e.g., another encoder 74 or a resistor), the seventh pin 100G may be the ground pin 100, the eighth pin 100H may correspond to the first LED 70 and/or the second LED 72, the ninth pin 100I be an additional shield pin 100, and/or the tenth pin 100J may correspond to the anode 71 of the detector 22. Additionally, it should be understood that the configuration of the connector 16 shown in FIGS. 8 and 9 may be adapted for use with any other suitable type of sensor 14, such as the EEG sensor 14C, for example.

Figure 10:
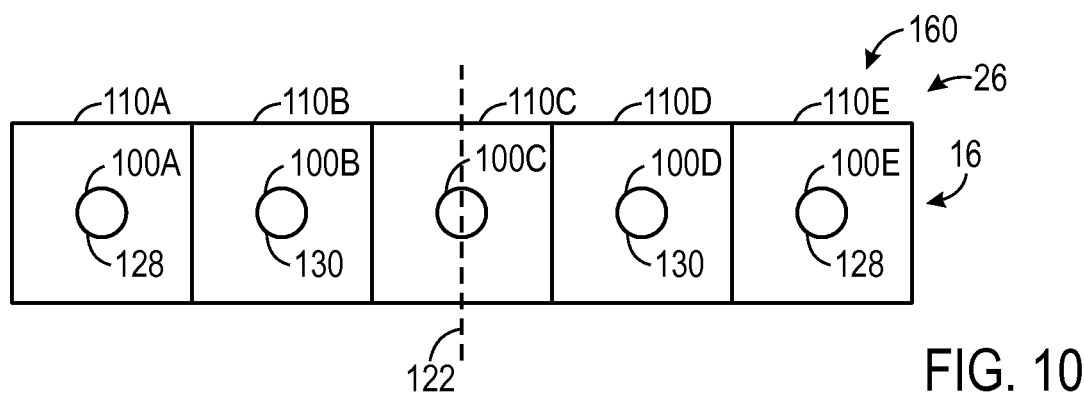
FIG. 10 is a schematic diagram of a connector having a one-dimensional array of five pins inserted within a receptacle of a monitor in a first orientation, in accordance with an embodiment.
Figure 11:
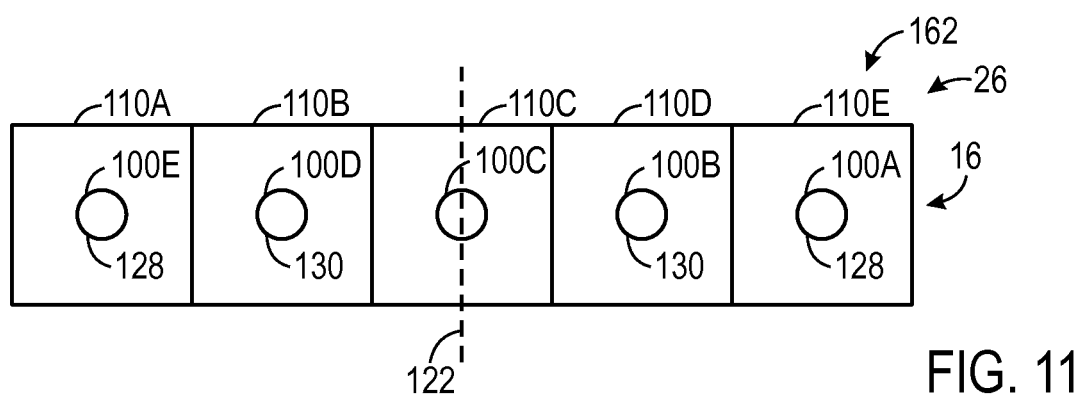
FIG. 11 is a schematic diagram of the connector of FIG. 10 inserted within the receptacle of the monitor in a second orientation, in accordance with an embodiment.

FIG. 10 is a schematic diagram of the connector 16 having a one-dimensional array of five pins 100 inserted within the sockets 110 of the receptacle 26 of the monitor 12 in a first orientation 160. FIG. 11 is a schematic diagram of the connector 16 of FIG. 10 inserted within the sockets 110 of the receptacle 26 of the monitor 12 in a second orientation 162. The connector 16 illustrated in FIG. 10 may be used with the pulse oximetry sensor 14A, for example. In such cases, one pin 100 may be coupled to the first LED 70 and/or to the second LED 72 and may be configured to transmit light drive signals from the monitor 12 when inserted into the receptacle 26, and another pin 100 may be coupled to the first LED 70 and/or second LED 72 and may be configured to transmit light drive signals from the monitor 12 when inserted into the receptacle 26. Additionally, one pin 100 may be coupled to the anode 71 of the detector 22 and another pin 100 may be coupled to the cathode 73 of the detector 22. As noted above, the pulse oximetry sensor 14A may also include the encoder 74, and in such cases, one pin 100 of the connector may be coupled to the encoder 74. The pins 100 may be arranged in functional pairs having 180 degree symmetry. For example, the first pin 100A and the fifth pin 100E may form the first functional pair 128, and the second pin 100B and the fourth pin 100D may form the second functional pair 130. The pins 100 of one of the functional pairs may be coupled to the anode 71 and the cathode 73 of the detector 22, while the pins 100 of another one of the functional pairs may be coupled to the first LED 70 and the second LED 72 of the emitter 20.

More particularly, in some embodiments, the first pin 100A may be coupled to the anode 71 of the detector 22, the fifth pin 100E may be coupled to the cathode 73 of the detector 22, the second pin 100B may be coupled to the first LED 70 and/or to the second LED 72 of the emitter 20, and the fourth pin 100D may be coupled to the first LED 70 and/or to the second LED 72 of the emitter 20. In the illustrated embodiment, the third pin 100C (e.g., center pin 100) may be coupled to the encoder 74 and is inserted into the third socket 110C regardless of the orientation of the connector 16 relative to the receptacle 26 of the monitor 12. Such a configuration may advantageously enable the monitor 12 to efficiently read the encoder 74 and determine the orientation of the connector 16 upon insertion of the connector 16 into the receptacle 26, as discussed in more detail below. Additionally, in some embodiments, instead of the central third pin 100C, a central terminal may be a coaxial style connector such as an MCX, MMCX, SMB, SMC suitable for low level signals such as the photodetector 22.

Additional pins 100 may be added to the one-dimensional array of pins 100 shown in FIGS. 10 and 11. For example, when six pins 100 are included in the one-dimensional connector 16, one pin 100 may be grounded or provided shielding. If the connector 16 is configured for use with regional saturation sensors 14B, additional pins 100 may be added for additional detectors 22 and/or additional emitters 20. In other embodiments, additional pins 100 may be added for calibration elements (e.g., the encoder 74 or a resistor), shielding, ground wire, and/or orientation detection, for example.

FIG. 12 is a schematic diagram of the connector 16 having a one-dimensional array of nine pins 100 inserted within the sockets 110 of the receptacle 26 of the monitor 12 in the first orientation 160. FIG. 13 is a schematic diagram of the connector 16 of FIG. 12 inserted within the sockets 110 of the receptacle 26 of the monitor 12 in the second orientation 162. The connector 16 has 180 degree symmetry and may be inserted into the receptacle 26 in either the first orientation 124 or the second orientation 126. As discussed above, in some embodiments, the pins 100 may be arranged in functional pairs that advantageously have 180 degree symmetry. For example, the first pin 100A and the ninth pin 100I may form the first functional pair 128, the second pin 100B and the eighth pin 100H may form the second functional pair 130, the third pin 100C and the seventh pin 100G may form the third functional pair 132, and the fourth pin 100D and the sixth pin 100F may form the fourth functional pair 134.

The connector 16 of FIGS. 12 and 13 may be used with any suitable sensor 14, including the pulse oximetry sensor 14A and the regional saturation sensor 14B. To facilitate discussion, the connector 16 of FIGS. 12 and 13 is discussed in the context of use with the EEG sensor 14C. The EEG sensor 14C includes one or more electrodes 52 for collecting the EEG signal. In certain embodiments, the EEG sensor 14C may include one electrode configured to function as a sensing electrode 52b, one electrode 52b configured to monitor artifacts resulting from muscular movement (e.g., via electromyography (EMG) signals), such as eye twitching, one electrode 52c configured to function as a grounding electrode, and one electrode 52d configured to function as a reference electrode. It should be noted that in certain embodiments, the EEG sensor 14C may be configured to perform EEG monitoring with fewer than four electrodes 52, or more than four electrodes 52. For example, in one embodiment, the EEG sensor 14C may be capable of performing EEG measurements without the electrode 52a for monitoring artifacts resulting from muscular movement. In other embodiments, such as where the EEG sensor 14C is a bilateral EEG sensor 14C, the electrodes 52 may include a reference electrode configured to be placed at the center of the patient's forehead, two electrodes each configured to be placed above an eye of the patient to monitor artifacts from eye twitching or movement, one ground electrode, and two electrodes each configured to be placed against the patient's temples for monitoring.

When used with the EEG sensor 14C, the connector 16 may have one or more pins 100 for transmitting the EEG signal from the sensing electrodes 52b, one or more pins 100 for transmitting an EMG signal from the artifact-monitoring electrodes 52a, one or more pins 100 for transmitting signals from reference electrodes 52d, and one or more pins coupled to the encoder 74 or other calibration element. In some embodiments, the connector 16 may have one or more pins 100 for shielding and/or one or more pins 100 connected to the ground electrode 52d. As discussed above, the pins 100 may advantageously be arranged in functional pairs having 180 degree symmetry. For example, a first pin 100A may provide shielding, a second pin 100B may be coupled to the encoder 74 or other calibration element, a third pin 100C may be coupled to the electrode 52 for obtaining the EEG signal, a fourth pin 100D may be coupled to the reference electrode 52, a fifth pin 100E may be a ground pin, a sixth pin 100F may be coupled to the reference electrode 52, a seventh pin 100G may be coupled to the electrode 52 for obtaining the EMG signal, the eighth pin 100H may be coupled to the encoder 74 or other calibration element, and the ninth pin 100I may provide shielding or be a spare pin. In the illustrated configuration, the fifth pin 100E is coupled to the fifth socket 110E, regardless of whether the connector 16 is in the first orientation 160 or the second orientation 162. In certain embodiments, the fifth pin 100E may be coupled to the encoder 74. Such a configuration may advantageously enable the monitor 12 to efficiently read the encoder 74 and determine the orientation of the connector 16 upon insertion of the connector 16 into the receptacle 26, as discussed in more detail below.

Figure 14:
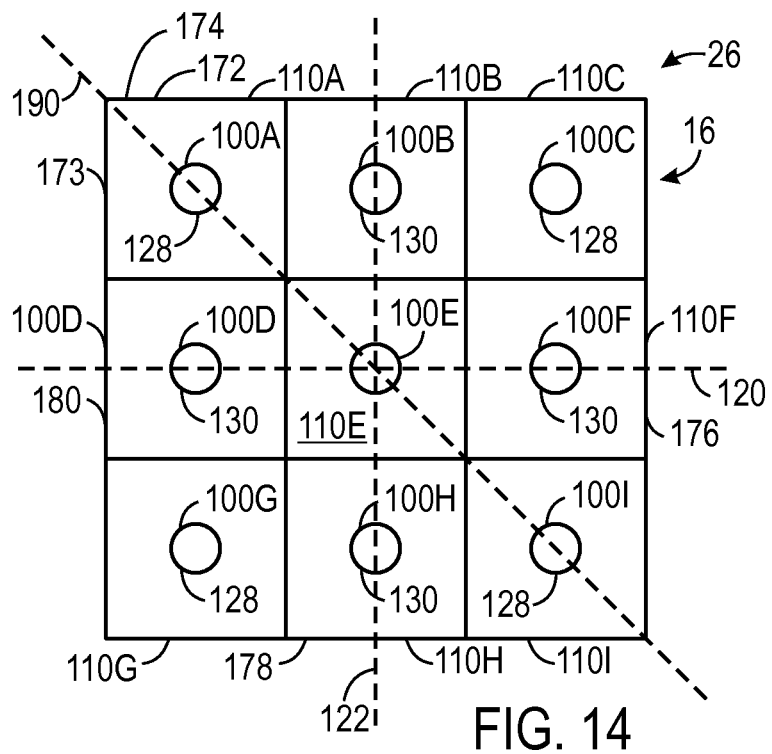
FIG. 14 is a schematic diagram of a multiple orientation connector having a two-dimensional array of nine pins arranged in a square shape and inserted within a receptacle of a monitor in a first orientation, in accordance with an embodiment.

FIG. 14 is a schematic diagram of the connector 16 having a two-dimensional array of nine pins 100 arranged in a square shape and inserted within the sockets 110 of the receptacle 26 of the monitor 12 in a first orientation 170. The connector 16 may have a housing 173 that has a square shape. Thus, the housing may be symmetrical about both the horizontal axis 120 and the vertical axis 122, and about a diagonal axis 190. The connector 16 of FIG. 14 may be configured to be inserted into the receptacle 26 in four different orientations (e.g., with a first side 172 of the housing 173 adjacent to a top side 174 of the receptacle 26, with a second side 176 of the housing 173 adjacent to the top side 174, with a third side 178 of the housing 173 adjacent to the top side 174, or with a fourth side 180 adjacent to the top side 174). In some such cases, the pins 100 may be arranged to have 90 degree symmetry. Additionally, in some embodiments, the pins 100 may be arranged into functional groups having 90 degree symmetry to facilitate the exchange of signals between the connector 16 and the receptacle 26 and to reduce software and/or hardware adjustments. For example, the first pin 100A, the third pin 100C, the seventh pin 100G, and the ninth pin 100I may form the first functional group 128, while the second pin 100B, the fourth pin 100D, the sixth pin 100F, and the eighth pin 100H form the second functional group 130. In the illustrated embodiment, the fifth pin 100E is a center pin that is inserted into the fifth socket 110E regardless of the orientation of the connector 16 relative to the receptacle 26. In some cases, the center pin 100, 182 may be coupled to the encoder 74. Such a configuration may advantageously enable the monitor 12 to efficiently read the encoder 74 and determine the orientation of the connector 16 upon insertion of the connector 16 into the receptacle 26, as discussed in more detail below.

As discussed above, the connector 16 may be inserted into the receptacle 26 in multiple different orientations relative to the receptacle 26, providing convenience in the medical setting. In some embodiments, the monitor 12 may include circuitry (e.g., the microprocessor 76) that is configured to determine the orientation of the connector 16. Furthermore, in certain embodiments, the circuitry of the monitor 12 may be configured to adjust hardware and/or software based on the determined orientation. Such steps enable reconfiguration of the internal circuitry of the monitor 12 and may enable the monitor 12 to provide proper signals to the sensor 14 and/or to properly process the signals received from the sensor 14, regardless of the orientation of the connector 16.

By way of example, with reference to the embodiments shown in FIGS. 6 and 7, the monitor 12 may determine whether the connector 16 is inserted into the receptacle 26 in the first orientation 124 or in the second orientation 126. The monitor 12 may adjust the light drive signals based on the determined orientation. For example, in configurations where the LED's 70, 72 are in a back-to-back configuration, the monitor 12 may provide a first light drive signal to illuminate the first LED 70 and then provide a second light drive signal to illuminate the second LED 72, if the connector 16 is in the first orientation 124. However, the monitor 12 may reverse the order in which the LED's 70, 72 are driven if the connector 16 is in the second orientation 126. In some such embodiments, the monitor 12 may not adjust the order in which the LED's 70, 72 are driven, but instead, may account for the orientation during demodulation and processing of the signals received by the detector 22.

By way of another example, in configurations where the LED's 70, 72 are not back-to-back but are instead directly coupled to different pins 100, the monitor 12 may send a first light drive signal via the third socket 110C of the receptacle 26 to the third pin 100C to illuminate the first LED 70, if the connector 16 is in the first orientation 124. However, if the connector 16 is in the second orientation 126, the monitor 12 may send a second light drive signal via the third socket 110C of the receptacle 26 to the eighth pin 100H to illuminate the second LED 72. As noted above, in the pulse oximetry sensor 14A or in the regional saturation sensor 14B, the first LED 70 may be an IR LED and the second LED 72 may be a red LED, and the monitor 12 may adapt to provide the proper light drive signals based on the orientation of the connector 16.

Figure 15:
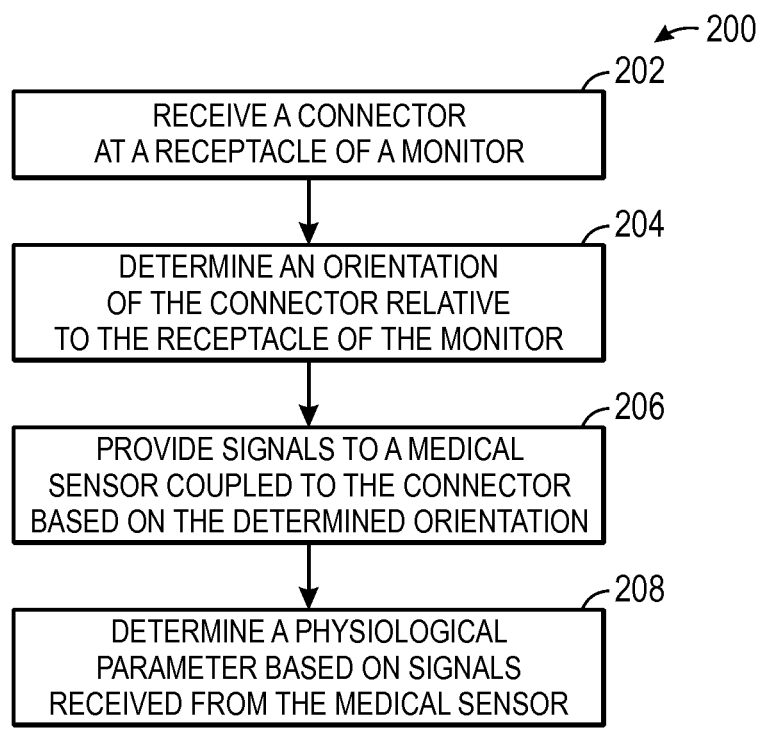
FIG. 15 is a process flow diagram of a method of determining a physiological parameter of a patient using a medical monitoring system having a multiple orientation connector, in accordance with an embodiment.

With the foregoing in mind, FIG. 15 is a process flow diagram of a method 200 of using a medical monitoring system (e.g., the pulse oximetry system 10, the regional saturation system 40, or the BIS system 50) having the connector 16 to determine a physiological parameter of a patient, in accordance with an embodiment. As shown in step 202, the receptacle 26 of the monitor 12 receives the connector 16. In certain embodiments, the monitor 12 may be configured to detect insertion of the connector 16 into the receptacle 26. Any suitable technique for detecting the presence of the connector 16 within the receptacle 26 may be utilized, such as mechanical, optical, or electrical switches, for example. In such cases, the monitor 12 may automatically carry out one or more prescribed steps to determine the orientation of the connector 16 after the connector 16 is detected within the receptacle 26. In other embodiments, an operator may couple the connector 16 to the receptacle 26 and may provide operator inputs to initiate a patient monitoring session. In such cases, once the operator input is received, the microprocessor 76 may determine the orientation of the connector 16 relative to the receptacle 26 prior to collecting patient data during the patient monitoring session.

While the connector 16 is inserted into the receptacle 26, the microprocessor 76 of the monitor 12 may determine the orientation of the connector 16 relative to the receptacle 26, at step 204. As discussed in detail below, the microprocessor 76 may be configured to determine the orientation of the connector 16 in any of a variety of suitable manners. For example, the microprocessor 76 may be configured to determine the orientation of the connector 16 based on interactions with the emitter 20, the detector 22, and/or the encoder 74 of the sensor 14. Additionally or alternatively, in certain embodiments, the monitor 12 may be configured to determine the orientation of the connector 16 based on crosstalk between pins 100 of the connector 16 and/or by interacting with the orientation element 121 provided on the connector 16.

After the orientation is determined, the microprocessor 76 may initiate the exchange of appropriate signals with the sensor 14 via the sockets 110 and the pins 100 of the connector 16, based on the determined orientation, at step 206. Additionally, the microprocessor 76 may process signals received from the sensor 14 based on the determined orientation. In certain embodiments, the microprocessor 76 may process the received signals to determine one or more physiological parameters, at step 208. As set forth above, the microprocessor 76 may be configured to determine any of a variety of physiological parameters, such as oxygen saturation, blood pressure, heart rate, regional saturation, and/or EEG.

Figure 16:
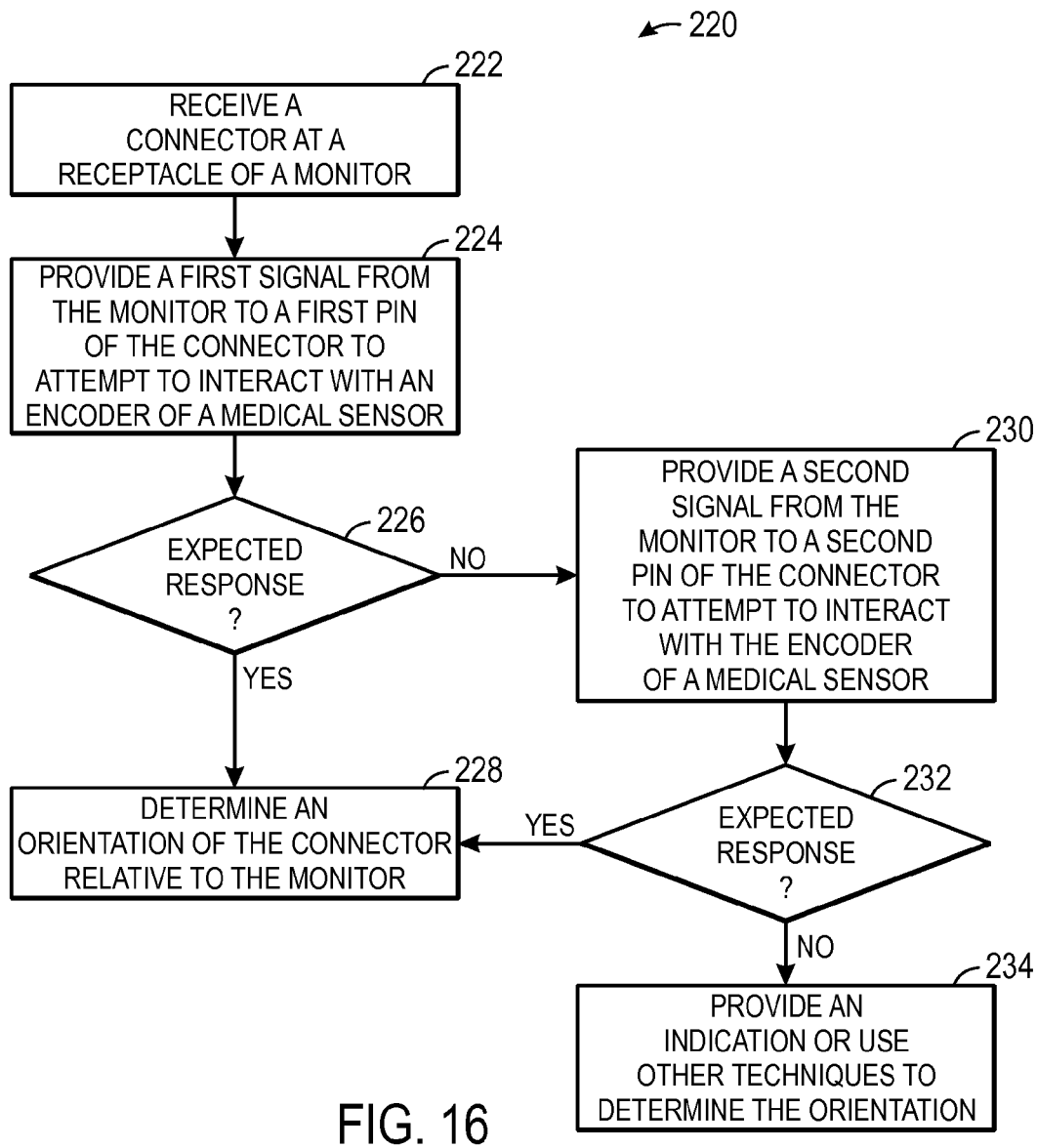
FIG. 16 is a process flow diagram of a method of determining an orientation of a multiple orientation connector relative to a receptacle of a monitor based on an interaction with an encoder of a medical sensor, in accordance with an embodiment.

Various methods of determining the orientation of the connector 16 are set forth in FIGS. 16-20. It should be understood that any combination of the one or more of the disclosed methods for determining the orientation of the connector 16 may be carried out simultaneously or sequentially. FIG. 16 is a process flow diagram of a method 220 of determining, using the microprocessor 76, an orientation of the connector 16 relative to the receptacle 26 based on an interaction with the encoder 74 of the sensor 14, in accordance with an embodiment. As shown, the receptacle 26 receives the connector 16 in any one of multiple suitable orientations, in step 222.

In step 224, the microprocessor 76 attempts to interact with the encoder 74 of the sensor 12 via one of the signal paths or channels (e.g., one of the pins 100 and corresponding socket 110). For example, the microprocessor 76 may provide a first signal to one pin 100 of the connector 16 to attempt to interact with the encoder 74. If the expected response from the encoder 74 is received at the microprocessor 76, at step 226, then the microprocessor 76 may determine the orientation of the connector 16, at step 228. If the expected response is not received, then the microprocessor 76 may determine that the channel is not in communication with the encoder 74. Thus, the microprocessor 76 may provide a second signal to another pin 100 of the connector 16 to attempt to interact with the encoder 74, at step 230. If the expected response from the encoder 74 is received at the microprocessor 76, at step 232, then the microprocessor 76 may determine the orientation of the connector 16. Additionally, in some embodiments, if the expected response is not received in step 226 or step 232, the microprocessor 76 may provide an indication that the orientation cannot be determined, such as via the display 28, and/or may attempt to determine the orientation via other techniques, such as those discussed below with respect to FIGS. 18-20, at step 234.

Furthermore, as set forth above, the pins 100 of the connector 16 may be arranged in functional pairs. For example, with reference to FIGS. 6 and 7, the second socket 110B and the fifth socket 110E may be designated encoder sockets 110. In such cases, the microprocessor 76 may provide a signal via one or both encoder sockets 110 to attempt to interact with the encoder 74. If one pin 100 does not provide the expected response, the microprocessor 76 may provide the signal via the other encoder socket 110 to attempt to interact with the encoder 74. The microprocessor 76 may attempt to communicate with the encoder 74 via both encoder sockets 110 simultaneously or in series (e.g. sequentially). In certain embodiments, the microprocessor 76 may be configured to attempt communication by passing signals through various channels in a certain predetermined order, or the microprocessor 76 may attempt communication with the encoder 74 based at least in part on the most recent orientation with which the connector 16 was inserted into the receptacle 26 (e.g., based on data stored in a memory of the monitor 12, such as the ROM 98 or RAM 96).

Additionally, as discussed above with respect to FIGS. 10 and 11 for example, the central pin 100 may be coupled to the encoder 74 to enable the monitor 12 to interact with the encoder 74 via the central socket 110 regardless of the orientation of the connector 16 relative to the receptacle 26. In such cases, interaction with the encoder 74 may not provide information related to the orientation of the connector 16, but rather, may enable efficient interaction with the encoder 74, which in turn, may provide information related to the type of the sensor 12, or other characteristics of the sensor 12 or the connector 16, that may be useful for patient monitoring and/or efficiently determining the orientation through other techniques set forth below.

Figure 17:
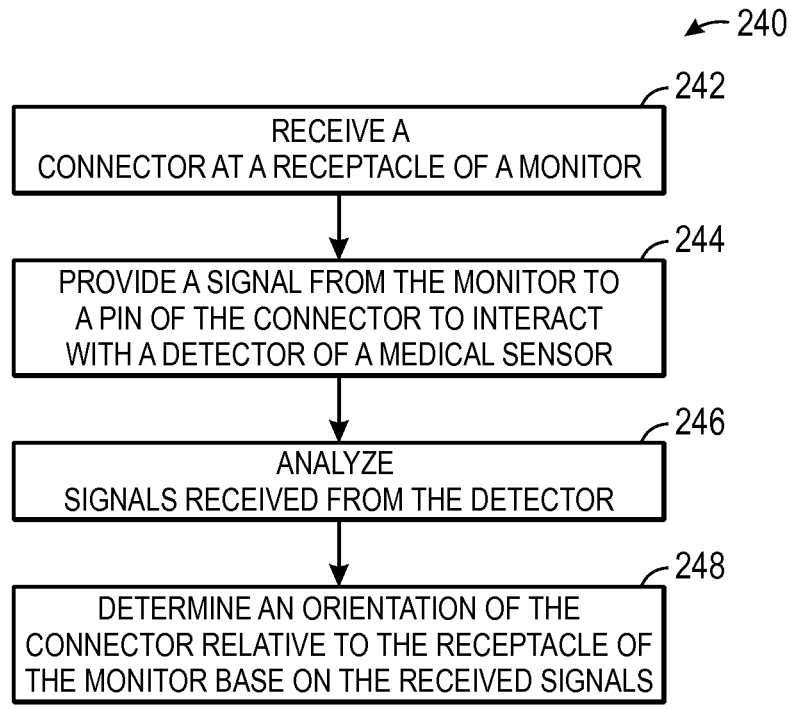
FIG. 17 is a process flow diagram of a method of determining an orientation of a multiple orientation connector relative to a receptacle of a monitor based on an interaction with a photodetector of a medical sensor, in accordance with an embodiment.

FIG. 17 is a process flow diagram of a method 240 of determining an orientation of the connector 16 relative to the receptacle 26 based on an interaction with the detector 22 of the sensor 14, in accordance with an embodiment. As shown in FIG. 17, at step 242, the receptacle 26 receives the connector 16 in any one of multiple suitable orientations. In step 244, the microprocessor 76 may attempt to interact with the detector 22 of the sensor 14 via one or more signal paths (e.g., one or more of the pins 100 and corresponding sockets 110). In particular, the microprocessor 76 may attempt to pass a current through the photodetector 22. For example, in embodiments where the pins 100 are arranged in functional pairs and the receptacle 26 has dedicated detector sockets 110, the microprocessor 76 may attempt to pass the current through the photodetector 22 via a first one of the dedicated detector sockets 110.

At step 246, the microprocessor 76 may analyze the signals received from the detector 22, such as via the dedicated detector sockets 110, for example. At step 248, the microprocessor 76 may determine the orientation of the connector 16 based on whether the signals indicate that the current passed through the photodetector 22. For example, if the current passes through the photodetector 22, then the microprocessor 76 may determine that the first one of the dedicated detector sockets 110 is coupled to the anode 71 of the photodetector 22. However, if the current does not pass through the photodetector 22, then the microprocessor 76 may determine that the first one of the dedicated detector sockets 110 is coupled to the cathode 73 of the photodetector 22. Based on this determination, the microprocessor 76 may determine how to appropriately process signals received from the photodetector 22. Additionally, such information may be used by the microprocessor 76 to determine the orientation of the connector 16 and may enable the microprocessor 76 to appropriately exchange signals with the sensor 14.

Figure 18:
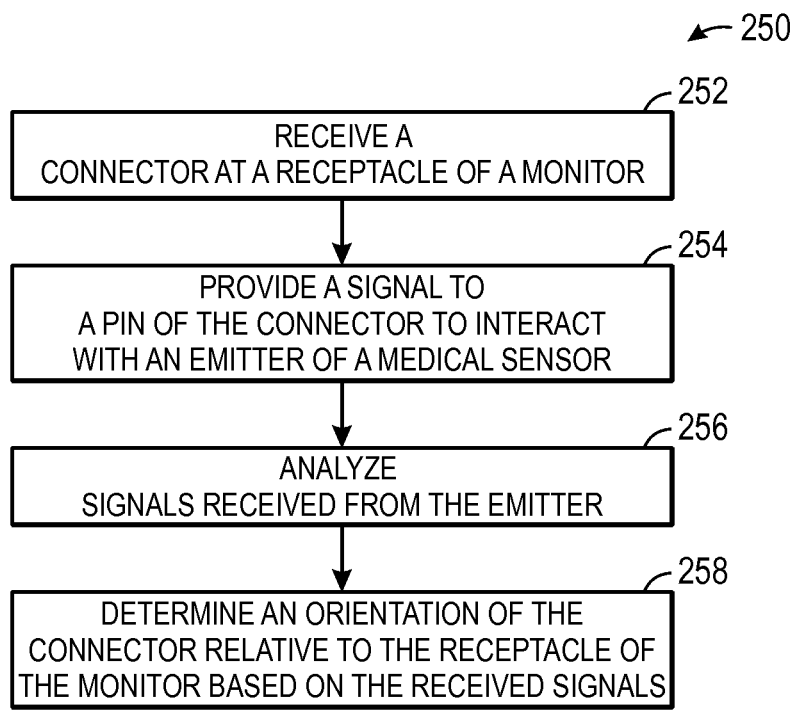
FIG. 18 is a process flow diagram of a method of determining an orientation of a multiple orientation connector relative to a receptacle of a monitor based on an interaction with an emitter of a medical sensor, in accordance with an embodiment.

FIG. 18 is a process flow diagram of a method 250 of determining an orientation of the connector 16 relative to the receptacle 26 based on an interaction with the emitter 20 of the sensor 14, in accordance with an embodiment. As shown in FIG. 18, at step 252, the receptacle 26 receives the connector 16 in any one of multiple suitable orientations. In step 254, the microprocessor 76 may attempt to interact with the emitter 20 of the sensor 14 via one or more signal paths (e.g., one or more of the pins 100 and corresponding sockets 110). In particular, the microprocessor 76 may attempt to measure a voltage drop across the emitter 20. For example, in embodiments where the pins 100 are arranged in functional pairs and the receptacle 26 has dedicated emitter sockets 110, the microprocessor 76 may attempt to pass a current from a first one of the dedicated emitter sockets 110. Thus, the current may pass through one of the first LED 70 or the second LED 72 of the emitter 22.

At step 246, the microprocessor 76 may analyze the signals received from the emitter 20 via the first one of the dedicated emitter sockets 110 to determine the voltage drop. At step 258, the microprocessor 76 may determine the orientation of the connector 16 based on the determined voltage drop. For example, if the voltage drop is between approximately 1 and 1.5 volts (V), then the microprocessor 76 may determine that the current passed through a red LED of the emitter 20. However, if the voltage drop is between approximately 1.6 and 2 V, then the microprocessor 76 may determine that the current passed through an IR LED of the emitter 20. In some such cases, the microprocessor 76 may compare the voltage drop to a table (e.g., a database) or values stored in a memory (e.g., the ROM 98 or RAM 96) of the monitor 12 to determine the type of LED through which the current passed. Determination of the voltage drop in this manner may enable the monitor 12 to determine the orientation of the sensor 14.

Furthermore, in certain cases, the microprocessor 76 may pass a current through two dedicated emitter sockets 110 to attempt to interact with both the first LED 70 and the second LED 72 of the emitter 20. The microprocessor 76 may attempt to interact with both the first LED 70 and the second LED 72 simultaneously or sequentially. The microprocessor 76 may analyze and/or compare the signals received from each of the first LED 70 and the second LED 72 to determine which of the LEDs is an IR LED and which of the LEDs is a red LED. For example, the LED having the relatively higher voltage drop may be determined to be the IR LED, while the LED having the relatively lower voltage drop may be determined to be the red LED. Once the voltage drop across one or both of the first LED 70 and the second LED 72 is determined, the microprocessor 76 may determine how to appropriately exchange signals with the emitter 20. Additionally, such information may be used by the microprocessor 76 to determine the orientation of the connector 16 and may enable the microprocessor 76 to appropriately exchange signals with the sensor 14.

Figure 19:
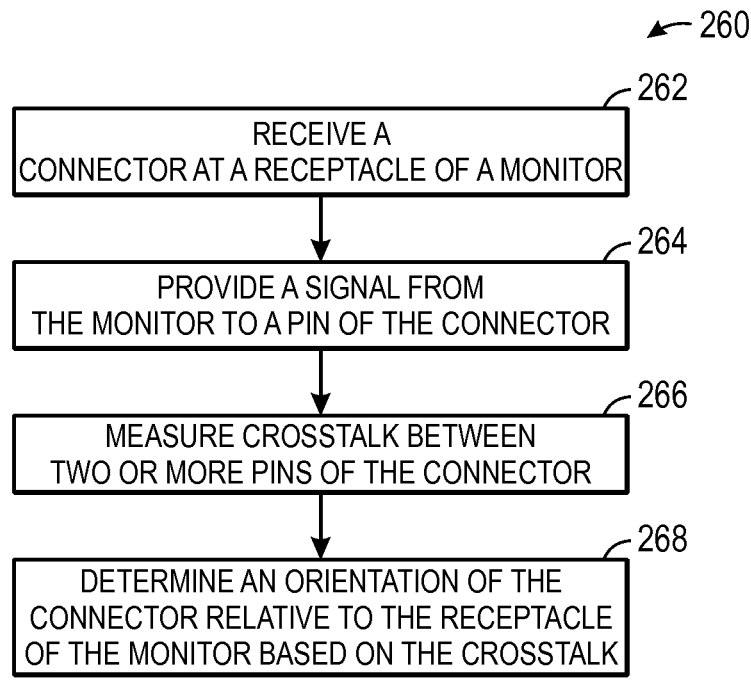
FIG. 19 is a process flow diagram of a method of determining an orientation of a multiple orientation connector relative to a receptacle of a monitor based on crosstalk between pins of the multiple orientation connector, in accordance with an embodiment.

FIG. 19 is a process flow diagram of a method 260 of determining an orientation of the connector 16 relative to the receptacle 26 based on crosstalk between pins 100 of the connector 16, in accordance with an embodiment. As shown in FIG. 19, at step 262, the receptacle 26 receives the connector 16 in any one of multiple suitable orientations. In step 254, the microprocessor 76 may generate signals along one or more signal paths (e.g., one or more of the pins 100 and corresponding sockets 110). For example, the microprocessor 76 may provide a light drive signal (e.g., a sinusoidal light drive signal) via one or more sockets 110, such as one or more dedicated emitter sockets 110. The microprocessor 76 may measure and/or analyze cross-talk received via other sockets 110 at step 256. Additionally, the microprocessor 76 may be configured to determine the orientation of the connector 16 based on the measured cross-talk at step 258.

Figure 20:
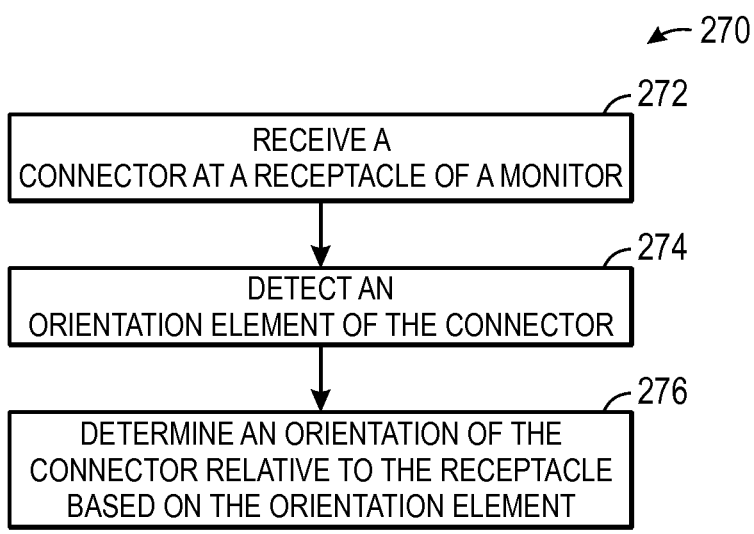
FIG. 20 is a process flow diagram of a method of determining an orientation of a multiple orientation connector relative to a receptacle of a monitor based on an interaction with an orientation element of the multiple orientation connector, in accordance with an embodiment.

FIG. 20 is a process flow diagram of a method 270 of determining an orientation of the connector 16 relative to the receptacle 26 based on detection of the orientation element 121, in accordance with an embodiment. As shown in FIG. 20, at step 272, the receptacle 26 receives the connector 16 in any one of multiple suitable orientations. In certain embodiments, the monitor 12 may be configured to detect the orientation element 121 of the connector 16 at step 274. As discussed above with respect to FIG. 5, any suitable technique for detecting the presence of the orientation element 121 at the receptacle 26 may be utilized, such as mechanical, optical, or electrical detection elements 123, 125 (e.g., sensors or switches), for example. At step 276, the microprocessor 76 may determine the orientation of the connector 16 based on the detected orientation element 121. For example, with reference to FIG. 5, if the orientation element 121 is detected by the first detection element 123 on a first side of the receptacle 26, then the microprocessor 76 may determine that the connector is in the first orientation 124. If the orientation element 121 is detected by the second detection element 125 on a second side of the receptacle 26, then the microprocessor 76 may determine that the connector 16 is in the second orientation 126.

Thus, the methods set forth above may include receiving the connector 16 at the receptacle 26 of the monitor 12, determining, using the processor 76 of the monitor 12, an orientation of the connector 16 relative to the receptacle 26 of the monitor 12, providing signals, using the processor 76, to the medical sensor 14 coupled to the connector 16 based on the determined orientation, and determining a physiological parameter based on signals received from the medical sensor 14. In some embodiments, determining the orientation of the connector 16 includes interacting with the encoder 74 of the medical sensor 14. In certain embodiments, determining the orientation of the connector 16 includes interacting with the emitter 20 of the medical sensor 14, and interacting with the emitter 20 includes measuring a voltage drop across the emitter 20. In certain embodiments, determining the orientation of the connector 16 includes interacting with the detector 22 of the medical sensor 14, and interacting with the detector 22 includes passing current through the detector 22. In certain embodiments, determining the orientation of the connector 16 includes measuring, using the processor 76, crosstalk between two or more pins 100 of the connector 16. In certain embodiments, determining the orientation of the connector 16 comprises detecting the orientation element 121 of the connector 16. The methods set forth herein may also include adjusting hardware or software of the monitor 12 to provide signals to the medical sensor 14 based on the determined orientation.

As indicated above, certain steps of the disclosed methods are carried out by the microprocessor 76 of the monitor 12. The microprocessor 76 may include one or more processing devices that access memory circuitry that includes one or more tangible, non-transitory, machine-readable media collectively storing instructions executable by the microprocessor 76 to perform the methods and control actions described herein. Such machine-readable media can be any available media that can be accessed by the microprocessor 76. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by the microprocessor 76. Machine-executable instructions comprise, for example, instructions and data which cause the microprocessor 76, or any monitor 12, multi-parameter monitor 32, general purpose computer, special purpose computer, or special purpose processing machines to perform a certain function or group of functions. As discussed above, the microprocessor 76 may execute instructions or code contained on the machine-readable or computer-readable storage medium to detect the orientation of the connector 16 and/or to appropriately interact with sensor 14 for patient monitoring, for example.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed.

Rather, the various embodiments may cover all modifications, equivalents, and alternatives falling within the spirit and scope of the disclosure as defined by the following appended claims.

What is claimed is:

1. A patient monitor for determining a physiological parameter of a patient, the patient monitor comprising:
   a receptacle connector configured to receive a corresponding plug connector for a medical sensor, wherein the receptacle connector is shaped to receive the corresponding plug connector in more than one orientation relative to the receptacle connector; and
   a processor electrically coupled to the receptacle connector and configured to interact with the corresponding plug connector or the medical sensor to determine the orientation of the corresponding plug connector.

2. The patient monitor of claim 1, wherein the processor is configured to interact with an emitter of the medical sensor, a detector of the medical sensor, an encoder of the medical sensor, or a combination thereof to determine the orientation of the corresponding plug connector.

3. The patient monitor of claim 1, wherein the processor is configured to measure crosstalk between pins of the corresponding plug connector to determine the orientation of the corresponding plug connector.

4. The patient monitor of claim 1, wherein the processor is configured to determine the orientation of the corresponding plug connector based on mechanical, optical, or electrical detection of an orientation element of the corresponding plug connector.

5. The patient monitor of claim 1, wherein the processor is configured to adjust hardware or software to provide signals to the medical sensor based on the determined orientation.

6. The patient monitor of claim 1, wherein the processor is configured to process signals received from the medical sensor based on the determined orientation.

7. The patient monitor of claim 1, wherein the receptacle connector comprises a central socket configured to interact with an encoder of the medical sensor while the corresponding plug connector is coupled to the receptacle connector.

8. A medical monitoring system comprising:
   a medical monitor; and
   a receptacle connector for coupling the medical monitor to a medical sensor, the receptacle connector comprising:
      a recess for receiving a corresponding plug connector; and
      a plurality of electrical contacts positioned within the recess and configured to electrically couple the monitor to the medical sensor when the plug connector is in a first orientation relative to the receptacle connector, and configured to electrically couple the monitor to the medical sensor when the plug connector is in a second orientation relative to the receptacle connector that is different from the first orientation;
   wherein the medical monitor comprises a processor electrically coupled to the receptacle connector and configured to determine the orientation of the corresponding plug connector based on signals received from the corresponding plug connector or the medical sensor, or a combination thereof.

9. The medical monitoring system of claim 8, wherein the medical monitor is configured to provide a first drive signal to illuminate a first light emitting diode of the medical sensor via a first electrical contact of the plurality of electrical contacts when the corresponding plug connector is inserted into the receptacle connector in the first orientation and is configured to provide a second drive signal to illuminate a second light emitting diode of the medical sensor via the first electrical contact of the plurality of electrical contacts when the corresponding plug connector is inserted into the receptacle connector in the second orientation.

10. The medical monitoring system of claim 9, wherein the medical monitor is configured to provide the first light drive signal to illuminate the first light emitting diode of the medical sensor via a second electrical contact of the plurality of electrical contacts when the corresponding plug connector is inserted into the receptacle of the monitor in the second orientation and is configured to transmit the second light drive signal to the second light emitting diode via the second electrical contact of the plurality of electrical contacts when the corresponding plug connector is inserted into the receptacle of the monitor in the first orientation.

11. The medical monitoring system of claim 10, wherein the first electrical contact and the second electrical contact are disposed in the receptacle connector with 180 degree symmetry relative to one another.

12. The medical monitoring system of claim 8, wherein the receptacle connector comprises at least two electrical contacts of the plurality of electrical contacts designated to interact with a detector of the medical sensor and at least two electrical contacts of the plurality of electrical contacts designated to interact with an emitter of the medical sensor.

13. The medical monitoring system of claim 8, wherein the medical monitor is configured to exchange signals with an encoder of the medical sensor via at least one electrical contact of the plurality of electrical contacts.

14. The medical monitoring system of claim 13, wherein the at least one electrical contact of the plurality of electrical contacts is a central contact that is configured to be coupled to the encoder while the corresponding plug connector is in the first orientation and in the second orientation.

15. A medical monitoring system comprising:
   a medical monitor; and
   a receptacle connector comprising a plurality of electrical contacts configured to electrically couple the medical monitor to a medical sensor when a plug connector is in a first orientation relative to the receptacle connector, and configured to electrically couple the monitor to the medical sensor when the plug connector is in a second orientation relative to the receptacle connector that is different from the first orientation;
   wherein the receptacle connector comprises two electrical contacts of the plurality of electrical contacts designated to interact with a detector of the medical sensor and two electrical contacts of the plurality of electrical contacts designated to interact with an emitter of the medical sensor.

16. The medical monitoring system of claim 15, wherein the two electrical contacts designated to interact with the detector are disposed with 180 degree symmetry relative to one another.

17. The medical monitoring system of claim 15, wherein the two electrical contacts designated to interact with the emitter are disposed with 180 degree symmetry relative to one another.

18. The medical monitoring system of claim 15, wherein the medical monitor is configured to exchange signals with an encoder of the medical sensor via one electrical contact of the plurality of electrical contacts, and the one electrical contact is positioned to enable the medical monitor to exchange signals with the encoder when the plug connector is in the first orientation and in the second orientation.

19. The medical monitoring system of claim 15, wherein the plurality of electrical contacts comprise a one-dimensional array of at least five electrical contacts.

20. The medical monitoring system of claim 15, wherein the medical monitor comprises a processor electrically coupled to the receptacle connector and configured to determine the orientation of the plug connector based on signals received from the medical sensor.

* * * * *